(12) United States Patent  
Van Gompel et al.

(10) Patent No.: US 8,167,861 B2
(45) Date of Patent: May 1, 2012

(54) DISPOSABLE GARMENT WITH STRETCHABLE ABSORBENT ASSEMBLY

(75) Inventors: Paul T. Van Gompel, Hortonville, WI (US); Nancy E. Dawson, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1764 days.

(21) Appl. No.: 10/879,323

(22) Filed: Jun. 29, 2004

(65) Prior Publication Data

US 2005/0143710 A1 Jun. 30, 2005

Related U.S. Application Data

(63) Continuation-in-part of application No. 10/750,253, filed on Dec. 31, 2003, now abandoned.

(51) Int. Cl.
*A61F 13/15* (2006.01)
*A61F 13/20* (2006.01)

(52) U.S. Cl. .................. 604/385.19; 604/385.22

(58) Field of Classification Search ............ 604/385.16, 604/378, 382, 385.19, 385.22
See application file for complete search history.

(56) References Cited

U.S. PATENT DOCUMENTS

| | | | |
|---|---|---|---|
| 2,931,361 A | 4/1960 | Sostrin | |
| 3,849,241 A | 11/1974 | Butin et al. | |
| 3,921,638 A | 11/1975 | Schaar | |
| 3,978,861 A | 9/1976 | Schaar | |
| 4,036,233 A | 7/1977 | Kozak | |
| 4,050,462 A | 9/1977 | Woon et al. | |
| 4,100,324 A | 7/1978 | Anderson et al. | |
| 4,205,679 A | 6/1980 | Repke et al. | |
| 4,522,874 A | 6/1985 | Pommez | |
| 4,560,372 A | 12/1985 | Pieniak | |
| 4,573,986 A | 3/1986 | Minetola et al. | |
| 4,631,062 A | 12/1986 | Lassen et al. | |
| 4,642,110 A | 2/1987 | Dudek | |
| 4,657,802 A | 4/1987 | Morman | |
| 4,663,220 A | 5/1987 | Wisneski et al. | |

(Continued)

FOREIGN PATENT DOCUMENTS

EP 0 217 032 A2 4/1987

(Continued)

OTHER PUBLICATIONS

Lakes, Roderic, Foam Structures with a Negative Poissons ratio, Science, 235, pp. 1038-1040.*

(Continued)

*Primary Examiner* — Melanie Hand
(74) *Attorney, Agent, or Firm* — Armstrong Teasdale LLP

(57) ABSTRACT

A disposable absorbent garment has an elastic inner layer having an interior surface for facing a wearer of the garment, and an exterior surface. The elastic inner layer has an elongate opening therein disposed at least within a crotch region of the garment, and is stretchable in at least a lateral direction of the garment. An outer layer of the garment is in opposed relationship with the elastic inner layer and is stretchable in at least the lateral direction of the garment. An absorbent assembly is secured to the elastic inner layer between the elastic inner layer and the outer layer and is sized larger than the opening of the elastic inner layer for underlying substantially the entire opening. The absorbent assembly is stretchable in at least the lateral direction of the garment for lateral stretching thereof in response to lateral stretching of the elastic inner layer.

38 Claims, 17 Drawing Sheets

U.S. PATENT DOCUMENTS

| | | | |
|---|---|---|---|
| 4,704,114 A | 11/1987 | Wilson et al. | |
| 4,704,116 A | 11/1987 | Enloe | |
| 4,710,187 A | 12/1987 | Boland et al. | |
| 4,720,415 A | 1/1988 | Vander Wielen et al. | |
| 4,731,066 A | 3/1988 | Korpman | |
| 4,747,846 A | 5/1988 | Bolond et al. | |
| 4,752,349 A | 6/1988 | Gebel | |
| 4,753,646 A | 6/1988 | Enloe | |
| 4,756,709 A | 7/1988 | Stevens | |
| 4,808,176 A | 2/1989 | Kielpikowski | |
| 4,834,736 A | 5/1989 | Boland et al. | |
| 4,846,823 A | 7/1989 | Enloe | |
| 4,854,995 A | 8/1989 | Kasper et al. | |
| 4,865,597 A | 9/1989 | Mason, Jr. et al. | |
| 4,874,451 A | 10/1989 | Boger et al. | |
| 4,892,536 A | 1/1990 | DesMarais et al. | |
| 4,935,021 A | 6/1990 | Huffman et al. | |
| 4,938,755 A | 7/1990 | Foreman | |
| 4,940,464 A | 7/1990 | Van Gompel et al. | |
| 4,990,147 A | 2/1991 | Freeland | |
| 5,026,364 A | 6/1991 | Robertson | |
| 5,037,416 A | 8/1991 | Allen et al. | |
| 5,046,272 A | 9/1991 | Vogt et al. | |
| 5,062,840 A | 11/1991 | Holt et al. | |
| 5,104,116 A | 4/1992 | Pohjola | |
| 5,108,385 A | 4/1992 | Snyder | |
| 5,114,781 A | 5/1992 | Morman | |
| 5,116,662 A | 5/1992 | Morman | |
| 5,151,092 A | 9/1992 | Buell et al. | |
| 5,224,405 A | 7/1993 | Pohjola | |
| 5,226,992 A | 7/1993 | Morman | |
| 5,269,775 A | 12/1993 | Freeland et al. | |
| 5,284,703 A | 2/1994 | Everhart et al. | |
| 5,295,987 A | 3/1994 | Widlund et al. | |
| 5,304,159 A | 4/1994 | Tanji et al. | |
| 5,340,424 A | 8/1994 | Matsushita | |
| 5,342,338 A | 8/1994 | Roe | |
| 5,342,342 A | 8/1994 | Kitaoka | |
| 5,344,516 A | 9/1994 | Tanji et al. | |
| 5,350,624 A | 9/1994 | Georger et al. | |
| 5,352,217 A | 10/1994 | Curro | |
| 5,356,405 A | 10/1994 | Thompson et al. | |
| 5,368,584 A | 11/1994 | Clear et al. | |
| 5,397,316 A | 3/1995 | LaVon et al. | |
| 5,397,317 A | 3/1995 | Thomas | |
| 5,439,459 A | 8/1995 | Tanji et al. | |
| 5,462,537 A | 10/1995 | Carr et al. | |
| 5,462,541 A | 10/1995 | Bruemmer et al. | |
| 5,486,166 A | 1/1996 | Bishop et al. | |
| 5,490,846 A | 2/1996 | Ellis et al. | |
| 5,496,429 A * | 3/1996 | Hasse et al. | 156/73.3 |
| 5,503,076 A | 4/1996 | Yeo | |
| 5,527,302 A | 6/1996 | Endres et al. | |
| 5,554,143 A | 9/1996 | Roe et al. | |
| 5,567,265 A | 10/1996 | Zajaczkowski | |
| 5,593,401 A | 1/1997 | Sosalla et al. | |
| 5,611,790 A | 3/1997 | Osborn, III et al. | |
| 5,624,422 A | 4/1997 | Allen | |
| 5,634,916 A | 6/1997 | Lavon et al. | |
| 5,643,240 A | 7/1997 | Jackson et al. | |
| 5,643,242 A | 7/1997 | Lavon et al. | |
| 5,645,542 A | 7/1997 | Anjur et al. | |
| 5,658,269 A | 8/1997 | Osborn, III et al. | |
| 5,681,302 A | 10/1997 | Melbye et al. | |
| 5,690,627 A | 11/1997 | Clear et al. | |
| 5,695,868 A | 12/1997 | McCormack | |
| 5,766,389 A | 6/1998 | Brandon et al. | |
| 5,779,690 A | 7/1998 | Gustafsson et al. | |
| 5,792,130 A | 8/1998 | Widlund et al. | |
| 5,804,021 A | 9/1998 | Abuto et al. | |
| 5,817,086 A | 10/1998 | Kling | |
| 5,820,973 A | 10/1998 | Dodge, II et al. | |
| 5,843,056 A | 12/1998 | Good et al. | |
| 5,846,232 A | 12/1998 | Serbiak et al. | |
| 5,873,868 A | 2/1999 | Nakahata | |
| 5,883,028 A | 3/1999 | Morman et al. | |
| 5,925,026 A | 7/1999 | Arteman et al. | |
| 5,928,211 A | 7/1999 | Gustafsson et al. | |
| 5,947,947 A | 9/1999 | Tanzer et al. | |
| 5,957,907 A | 9/1999 | Sauer | |
| 5,964,743 A | 10/1999 | Abuto et al. | |
| 5,997,981 A | 12/1999 | McCormack et al. | |
| 5,998,696 A | 12/1999 | Schone | |
| 6,022,607 A | 2/2000 | James et al. | |
| 6,049,915 A | 4/2000 | Malowaniec | |
| 6,077,254 A | 6/2000 | Silwanowicz et al. | |
| 6,093,870 A | 7/2000 | Carlsson | |
| 6,103,953 A | 8/2000 | Cree et al. | |
| 6,120,485 A | 9/2000 | Gustafsson et al. | |
| 6,129,720 A * | 10/2000 | Blenke et al. | 604/385.16 |
| 6,132,409 A | 10/2000 | Vogt et al. | |
| 6,132,411 A | 10/2000 | Huber et al. | |
| 6,149,638 A | 11/2000 | Vogt et al. | |
| 6,149,934 A | 11/2000 | Krzysik et al. | |
| 6,152,906 A | 11/2000 | Faulks et al. | |
| 6,152,907 A | 11/2000 | Widlund et al. | |
| 6,152,908 A | 11/2000 | Widlund et al. | |
| 6,160,197 A | 12/2000 | Lassen et al. | |
| 6,168,583 B1 | 1/2001 | Tanji et al. | |
| 6,174,303 B1 | 1/2001 | Suprise et al. | |
| 6,186,996 B1 | 2/2001 | Martin | |
| 6,193,701 B1 | 2/2001 | Van Gompel et al. | |
| 6,217,563 B1 | 4/2001 | Van Gompel et al. | |
| 6,231,557 B1 | 5/2001 | Krautkramer et al. | |
| 6,262,311 B1 | 7/2001 | Maassen et al. | |
| 6,262,331 B1 | 7/2001 | Nakahata et al. | |
| 6,264,639 B1 | 7/2001 | Sauer | |
| 6,264,641 B1 | 7/2001 | Van Gompel et al. | |
| 6,274,218 B1 | 8/2001 | Shimizu | |
| 6,312,786 B1 | 11/2001 | Schwinn | |
| 6,362,389 B1 | 3/2002 | McDowall et al. | |
| 6,409,711 B1 | 6/2002 | Jonbrink | |
| 6,413,247 B1 | 7/2002 | Carlucci et al. | |
| 6,454,750 B1 | 9/2002 | Vogt et al. | |
| 6,461,338 B1 | 10/2002 | Shimoe et al. | |
| 6,482,191 B1 * | 11/2002 | Roe et al. | 604/385.01 |
| 6,521,811 B1 | 2/2003 | Lassen et al. | |
| 6,552,245 B1 | 4/2003 | Roessler et al. | |
| 6,570,056 B1 | 5/2003 | Tanzer et al. | |
| 6,572,598 B1 | 6/2003 | Ashton et al. | |
| 6,582,413 B2 | 6/2003 | Krautkramer et al. | |
| 6,582,414 B1 | 6/2003 | Richardson | |
| 6,595,972 B1 | 7/2003 | Wise et al. | |
| 6,610,383 B1 | 8/2003 | Morman et al. | |
| 6,623,465 B1 | 9/2003 | Roe et al. | |
| 6,632,212 B1 | 10/2003 | Morman et al. | |
| 6,641,568 B2 | 11/2003 | Ashton et al. | |
| 6,641,570 B2 | 11/2003 | Mishima et al. | |
| 6,645,190 B1 | 11/2003 | Olson et al. | |
| 6,667,424 B1 | 12/2003 | Hamilton et al. | |
| 6,679,869 B1 | 1/2004 | Schlinz et al. | |
| 6,680,423 B1 | 1/2004 | Tanzer | |
| 6,682,512 B2 | 1/2004 | Uitenbroek et al. | |
| 6,695,827 B2 | 2/2004 | Chen et al. | |
| 6,702,799 B2 | 3/2004 | Otsubo | |
| 6,702,800 B1 | 3/2004 | Vukos et al. | |
| 6,703,538 B2 | 3/2004 | Lassen et al. | |
| 6,706,028 B2 | 3/2004 | Roe et al. | |
| 6,733,484 B2 | 5/2004 | Van Gompel et al. | |
| 6,755,808 B2 | 6/2004 | Balogh et al. | |
| 7,011,653 B2 | 3/2006 | Imsangjan et al. | |
| 2001/0014796 A1 | 8/2001 | Mizutani et al. | |
| 2001/0016719 A1 | 8/2001 | Mishima | |
| 2001/0023342 A1 | 9/2001 | Suekane | |
| 2002/0004350 A1 | 1/2002 | Morman et al. | |
| 2002/0013563 A1 | 1/2002 | Lassen et al. | |
| 2002/0029029 A1 | 3/2002 | Otsubo | |
| 2002/0052590 A1 | 5/2002 | Zehner et al. | |
| 2002/0058922 A1 | 5/2002 | Skog | |
| 2002/0072726 A1 | 6/2002 | Mishima et al. | |
| 2002/0099352 A1 | 7/2002 | Heden et al. | |
| 2002/0104608 A1 | 8/2002 | Welch et al. | |
| 2002/0111598 A1 | 8/2002 | Vogt et al. | |
| 2002/0165514 A1 | 11/2002 | Datta et al. | |
| 2002/0165517 A1 | 11/2002 | Datta et al. | |
| 2003/0004487 A1 | 1/2003 | Gompel et al. | |
| 2003/0023213 A1 | 1/2003 | Fernfors et al. | |

| | | | |
|---|---|---|---|
| 2003/0088230 A1 | 5/2003 | Balogh et al. | |
| 2003/0120243 A1 | 6/2003 | Uitenbroek et al. | |
| 2003/0125696 A1 | 7/2003 | Morman et al. | |
| 2004/0013850 A1 | 1/2004 | Kling | |
| 2004/0044323 A1 | 3/2004 | Roessler et al. | |
| 2004/0102749 A1 | 5/2004 | Olson et al. | |
| 2004/0127878 A1 | 7/2004 | Olson et al. | |
| 2004/0127881 A1 | 7/2004 | Stevens et al. | |
| 2004/0162538 A1 | 8/2004 | Mueller et al. | |
| 2005/0143710 A1 | 6/2005 | Van Gompel et al. | |
| 2005/0148987 A1 | 7/2005 | van Gompel et al. | |

FOREIGN PATENT DOCUMENTS

| | | |
|---|---|---|
| EP | 0 433 951 A2 | 6/1991 |
| EP | 0 603 748 A1 | 6/1994 |
| EP | 605 017 A2 | 7/1994 |
| EP | 0 835 088 B1 | 4/1998 |
| EP | 847 739 A2 | 6/1998 |
| EP | 0 951 886 A1 | 10/1999 |
| EP | 0 962 207 A2 | 12/1999 |
| EP | 1201212 A2 | 5/2002 |
| EP | 1 212 999 A2 | 6/2002 |
| EP | 1 219 274 A1 | 7/2002 |
| EP | 0 957 868 B1 | 2/2003 |
| EP | 1 310 224 A2 | 5/2003 |
| GB | 2 284 538 A | 6/1995 |
| GB | 2 305 610 A | 9/1996 |
| GB | 2 310 606 A | 9/1997 |
| GB | 2 325 146 A | 11/1998 |
| GB | 2 340 403 A | 2/2000 |
| JP | 2004 195244 A | 7/2004 |
| WO | WO 93/05742 | 4/1993 |
| WO | WO 93/06805 A1 | 4/1993 |
| WO | WO 95/15410 A1 | 6/1995 |
| WO | WO 95/19753 A1 | 7/1995 |
| WO | WO 98/29239 A1 | 7/1998 |
| WO | WO 99/33426 A1 | 7/1999 |
| WO | WO 99/33427 A1 | 7/1999 |
| WO | WO 00/37009 A3 | 6/2000 |
| WO | WO 01/88245 A2 | 11/2001 |
| WO | WO 02/34184 | 5/2002 |
| WO | WO 02/069870 A2 | 9/2002 |
| WO | WO 02/096333 A2 | 12/2002 |
| WO | WO 03/051254 A2 | 6/2003 |
| WO | WO 03/057106 A1 | 7/2003 |
| WO | WO 2004/108041 A1 | 12/2004 |

OTHER PUBLICATIONS

International Search Report for PCT/US2004/036762, dated Mar. 4, 2005, 5 pages.
International Search Report and Written Opinion for International Application No. PCT/US2004/004724, dated Aug. 3, 2004, 12 Pages.
"Polyethylene—Low Density (LDPE)—Material Information," Internet web page "http://www.goodfellow.com/csp/active/STATIC/E/Polyethylene_-_Low_Density.HTML", p. 3, line 1, Goodfellow Corporation, Devon, PA.

* cited by examiner

DISPOSABLE GARMENT WITH STRETCHABLE ABSORBENT ASSEMBLY

CROSS-REFERENCE TO RELATED APPLICATIONS

This application is a continuation-in-part of U.S. patent application Ser. No. 10/750,253 filed Dec. 31, 2003, the entire disclosure of which is incorporated herein by reference.

BACKGROUND OF THE INVENTION

Disposable garments, including disposable absorbent garments, have been known for decades. Disposable garments may include garments worn like underpants for children and adults, garments worn like training pants for toddlers and garments worn like diapers for infants. Disposable absorbent garments designed to absorb and contain bodily fluids may include adult/child incontinence garments, toddler training pants and infant diapers. "Disposable" is generally understood to mean something that has a limited period of use before its ability to perform its intended function is exhausted. With regard to garments, "disposable" garments typically are not constructed to withstand laundering.

Typically, it is desirable for disposable garments to fit close to the body of the wearer for comfort and discretion. The disposable garment may have or form an opening that fits around the user's waist, as well as two openings that fit around the user's legs. The disposable garment typically includes a front waist region, a back waist region and a crotch region that extends between and connects the front and back waist regions. The front waist region includes the portion of the disposable garment that, when worn, is positioned on the front of the user while the back waist region includes the portion of the disposable garment that, when worn, is positioned on the back of the user. The crotch region of the disposable garment includes the portion of the disposable garment that, when worn, is positioned between the legs of the user and covers the lower torso of the user. Disposable garments may include one or more layers of materials, such as nonwoven materials. For example, a disposable garment may include a liner material that forms the layer of material closest to the user's skin and an outer material that forms the layer of material closest to the user's other clothing. Disposable garments may also include features that improve how well the garments fit the user. For example, disposable garments may include stretchable, such as elastic, materials near the waist opening and leg openings of the garment to improve the fit of the garment around the user's waist and legs. Additionally, disposable garments may include fasteners that assist with securing the position of the garment in use. For example, disposable garments may include adhesive or mechanical fasteners to assist with securing the garments around the waists of the users. Disposable garments may include additional features that improve the fit range (i.e. the range of users able to wear a particular size of absorbent garment) of the garments.

Disposable absorbent garments may be similar to disposable garments and provide the ability to absorb and contain bodily fluids such as urine, feces and menses. In addition to one or more layers of materials similar to disposable garments, disposable absorbent garments may also include an absorbent material. For example, if a disposable absorbent garment includes a single layer of material, the absorbent material may be located on the side of the single layer of material that will be positioned closest to the user's skin during wear. A representative example of a commonly used disposable absorbent garment is a disposable diaper to be used by an infant or toddler. Disposable diapers may have various shapes when they are open or unfastened and laying generally flat. For example, disposable diapers may have an overall rectangular shape, T-shape, I-shape or hourglass shape. Disposable absorbent garments, such as infant diapers, have a longitudinal direction that generally corresponds to the length of the garments and a lateral direction that generally corresponds to the width of the garments. Disposable absorbent garments typically include at least four edges: a pair of laterally opposed side edges and a pair of longitudinally opposed waist edges. Disposable absorbent garments may include an interior surface that is configured to contact the user's skin during wear and an exterior surface opposite the interior surface that is configured to contact the user's clothing during wear.

Presently available disposable diapers include at least three layers: a substantially liquid impermeable outer cover (a.k.a. a "backsheet"), a liquid permeable bodyside liner (a.k.a. a "topsheet") that can be connected to the outer cover in a superposed relation and an absorbent core (or absorbent "body") that is located between the outer cover and the bodyside liner. The side edges of the outer cover generally define the laterally opposed side edges of the disposable diaper and the side edges may form curvilinear leg openings when the disposable diaper is worn. The waist edges of the outer cover generally define the waist edges of the disposable diaper and typically form the waist opening that is configured to encircle the waist of the user when the disposable absorbent garment is worn. The absorbent core is configured to contain and/or absorb body exudates discharged from the user. Presently-available disposable diapers typically include waist elastics, leg elastics and containment flaps. Presently-available disposable diapers further include adhesive tape fasteners or refastenable mechanical fasteners (or combinations of both) for releasably engaging the opposed side edges of the disposable diaper in the opposite waist regions. The mechanical fasteners can include a variety of materials and surfaces known for mechanical engagement such as buttons, pins, snaps, cohesives, mushroom-and-loop fasteners and hook and loop fasteners. Many disposable diapers also include an attachment panel located on the front or back waist region, opposite the fasteners to which the fasteners can be releasably engaged while the disposable diaper is worn.

While disposable garments and disposable absorbent garments have been known for many years, the materials used to construct them have continuously evolved as a result of new technologies for formulating and manufacturing disposable materials. Materials may be selected for performance or to provide a cost advantage, particularly given that many manufacturers produce disposable garments and disposable absorbent garments in very large quantities. One aspect of evolution has been the development and availability of stretchable materials to replace previously non-stretchable components in order to provide improvements in the way in which the garments fit and improvements in the range of fit of the garments. An example of a stretchable material for use in disposable garments is a necked bonded laminate material (hereinafter "NBL material"). One of the first uses identified for a stretchable material, such as a NBL material, in the construction of a disposable diaper was as an "ear" material where the "ear" was attached to the longitudinal side edge of the diaper in the back waist region and to which was attached a mechanical fastener engageable with the front waist region.

Stretchable materials may include materials that are extensible and materials that are elastic. "Extensible" materials typically have lower capacities to retract to their original lengths after stretching while "elastic" materials typically have a greater range of stretch and come close to completely retracting to their original lengths after stretching.

With the advent of the availability of stretchable materials to construct disposable absorbent garments, various configurations for garments incorporating stretchable materials have been described. For example, once a stretchable material is selected to form a component of a garment, the material may be modified to provide a range of stretch characteristics. U.S. Pat. No. 6,193,701 (hereinafter "the '701 patent") describes personal care articles that may include resiliently stretchable outer covers and/or resiliently stretchable bodyside liners. The '701 patent describes that the resiliently stretchable materials may be "embossed" to modify the "resistance to stretch" properties. The "embossments" may be used to reduce or otherwise control the stretching of different portions or "zones" of the garments. Therefore, in addition to stretchable materials themselves being available for use in absorbent garments, the potential for some forms of modification of the stretch properties has also been described.

In addition to garments utilizing extensible and otherwise stretchable materials, garments utilizing elastic materials have been described. International Publication No. WO 02/34184 (hereinafter "the 34184 publication") describes absorbent garments that may have a biaxially stretchable outer cover and a biaxially stretchable bodyside liner. The "biaxially stretchable" materials described as being suitable in the 34184 publication include elastic materials capable of stretching in at least two directions.

Simultaneous with the development of stretchable materials having lower cost and/or improved properties for use in disposable garments, developments with regard to the structural features of disposable garments have also occurred. Just as stretchable ears were developed to improve the fit of garments, other features have been developed to improve the waste containment function of the garments. An example of one such class of features is the provision of holes or apertures between layers of the garments to separate the waste materials from the wearer's skin. More specific examples of such features are apertures or openings in the bodyside liners of disposable absorbent garments that are provided to separate solid wastes from the wearer's skin to reduce the incidence of troublesome conditions such as diaper rash.

Even though significant and numerous advancements have occurred in the materials and structural features available for the construction of disposable garments, there remain opportunities for improvement in the fit and containment capacity of such garments. For example, there remains a need for a disposable garment that provides excellent fit on the wearer that results in reduced leakage and that provides a barrier between the wearer's skin and the waste materials being contained by the garment. Additionally, there remains a need for a disposable garment that has a simplified construction and that eliminates the attachment of multiple separate components that increase the cost and complicate the manufacture of disposable garments.

SUMMARY OF THE INVENTION

In general, a disposable absorbent garment according to one embodiment of the present invention has a longitudinal direction, a lateral direction, a front waist region, a back waist region and a crotch region extending longitudinally between and interconnecting the front waist region and the back waist region. The garment also has longitudinal ends and lateral side edges and comprises an elastic inner layer having an interior surface for facing a wearer of the garment, and an exterior surface. The elastic inner layer has an elongate opening therein disposed at least within the crotch region of the garment, and is stretchable in at least the lateral direction of the garment. An outer layer of the garment is in opposed relationship with the elastic inner layer and is stretchable in at least the lateral direction of the garment.

An absorbent assembly is disposed between the elastic inner layer and the outer layer for receiving body waste that passes through the elastic inner layer. The absorbent assembly is secured to the elastic inner layer and is sized larger than the opening of the elastic inner layer for underlying substantially the entire opening. The absorbent assembly is stretchable in at least the lateral direction of the garment for lateral stretching thereof in response to lateral stretching of the elastic inner layer.

In another embodiment, a disposable absorbent garment has a longitudinal direction, a lateral direction, a front waist region, a back waist region and a crotch region extending longitudinally between and interconnecting the front waist region and the back waist region. The garment also has longitudinal ends and lateral side edges and generally comprises an elastic inner layer having an interior surface for facing a wearer of the garment, and an exterior surface. The elastic inner layer has an elongate opening therein disposed at least within the crotch region of the garment and is stretchable in at least the lateral direction of the garment.

An absorbent assembly is secured to the elastic inner layer and is sized larger than the opening of the elastic inner layer. The absorbent assembly also underlies substantially the entire opening of the elastic inner layer and comprises comprising a liquid permeable topsheet layer, a barrier layer in opposed relationship with the topsheet layer, and an absorbent core layer disposed between the topsheet layer and the barrier layer. The absorbent assembly is stretchable in at least the lateral direction for lateral stretching of the absorbent assembly in response to lateral stretching of the elastic inner layer.

In yet another embodiment, a disposable absorbent garment has a longitudinal direction, a lateral direction, a front waist region, a back waist region and a crotch region extending longitudinally between and interconnecting the front waist region and the back waist region. The garment also has longitudinal ends and lateral side edges and generally comprises an elastic inner layer having an interior surface for facing a wearer of the garment, and an exterior surface. The elastic inner layer has an elongate opening therein disposed at least within the crotch region of the garment, and is stretchable in at least the lateral direction of the garment. An outer layer of the garment is in opposed relationship with the elastic inner layer and is stretchable in at least the lateral direction of the garment.

An absorbent assembly is disposed between the elastic inner layer and the outer layer for receiving body waste that passes through the elastic inner layer, and is secured to the elastic inner layer. The absorbent assembly is sized larger than the opening of the elastic inner layer for underlying substantially the entire opening. The absorbent assembly is stretchable in at least the lateral direction of the garment for lateral stretching thereof in response to lateral stretching of the elastic inner layer.

At least one leg elastic member is located generally adjacent each of the laterally opposite side edges of the garment and extends longitudinally along the garment side edges. A reinforcement element is secured to the elastic inner layer generally at the opening thereof and is elastic in at least the lateral direction of the garment.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

The present disclosure of the invention will be expressed in terms of its various components, elements, constructions, configurations, arrangements and other features that may also be individually or collectively be referenced by the term, "aspect(s)" of the invention, or other similar terms. It is contemplated that the various forms of the disclosed invention may incorporate one or more of its various features and aspects, and that such features and aspects may be employed in any desired, operative combination thereof.

It should also be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The disposable absorbent garments of the present invention will be described in terms of a disposable absorbent garment that is adapted to be worn by infants about the lower torso, that is, a disposable absorbent garment that is similar to a disposable diaper. It is understood that the features of the present invention are equally adaptable for other types of disposable absorbent garments such as adult incontinence garments, training pants, disposable swim pants and feminine hygiene garments.

Figure 1:
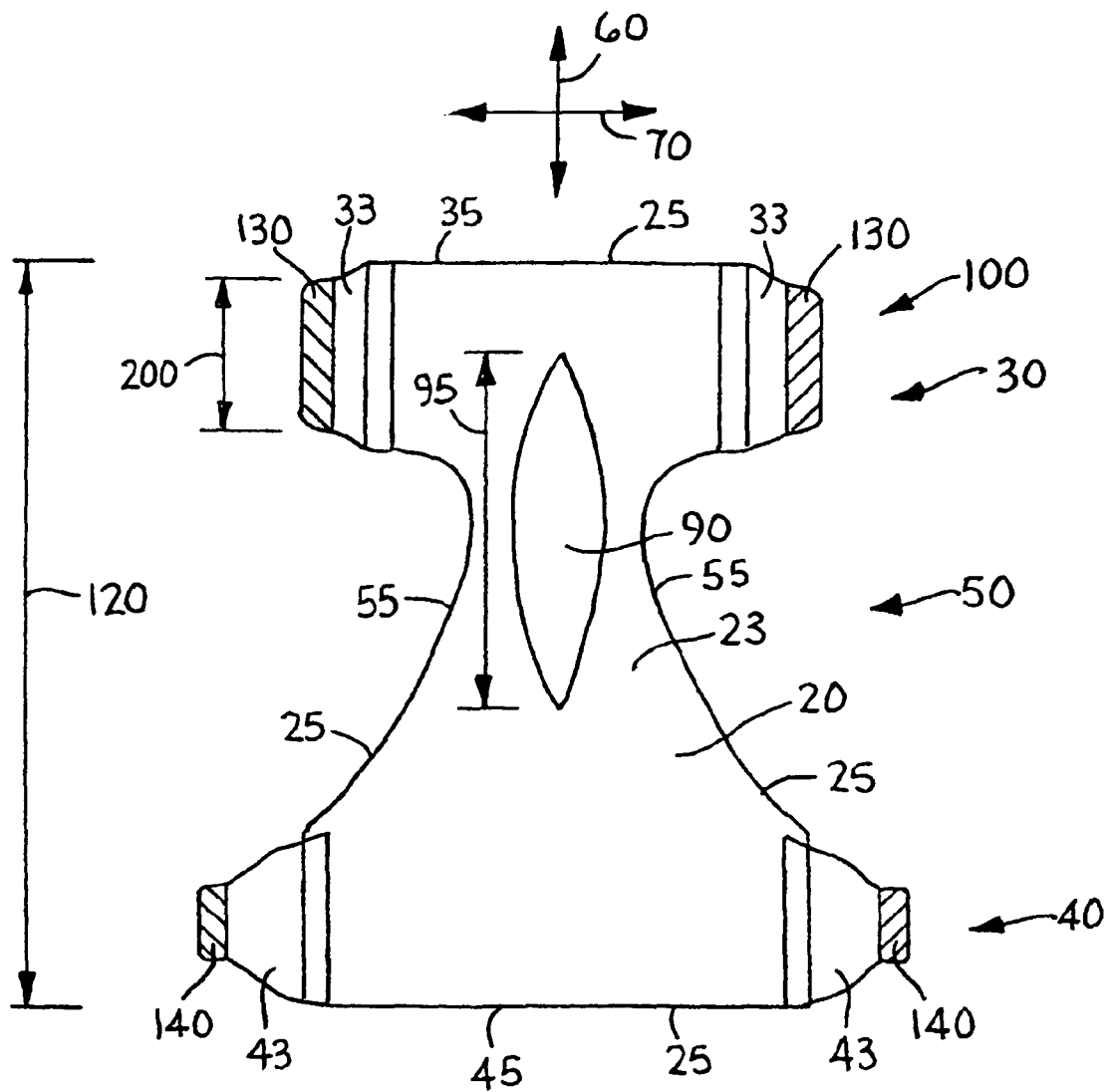
FIG. 1 representatively shows a plan view of an example of a disposable absorbent garment of the present invention (a garment to be worn by an infant/toddler) in an unfastened and laid flat condition with the surface of the garment that contacts the wearer's skin facing the viewer.

FIG. 1 representatively illustrates a disposable garment of the present invention, generally indicated at 100, in a flat, laid-out configuration. The disposable garment 100 has a front waist region 30, a back waist region 40 and a crotch region 50 extending longitudinally between and interconnecting the front and back waist regions. The garment 100 also has a longitudinal direction 60 oriented along the length of the garment and a lateral direction 70 oriented perpendicular to the longitudinal direction and across the width of the garment. In the illustrated embodiment, the garment 100 comprises an inner layer 20 having an interior, bodyfacing surface and an exterior surface, and an absorbent assembly, generally indicated at 150 (FIG. 2), secured to the exterior surface of the inner layer for absorbing body exudates. In a particularly suitable embodiment, the inner layer 20 is constructed of an elastic material such that the elastic inner layer is elastically stretchable in the lateral direction 70. It is contemplated that the inner layer may instead, or may additionally, be elastically stretchable in the longitudinal direction 60. The term "stretchable" as used herein may include materials that are extensible and materials that are elastic. "Extensible" materials typically have lower capacities to retract to their original lengths after stretching while "elastic" materials typically have a greater range of stretch and come close to completely retracting to their original lengths after removal of an elongating force.

Various materials may be used to construct the elastic inner layer 20. For example, various nonwoven materials are known that may be elastically stretchable in a machine direction (typically, the same as the longitudinal direction 60 of the garment 100) or a cross direction (which may be the same as the lateral direction 70 of the garment 100), or both. Suitable nonwoven materials include elastic nonwoven materials and laminates of nonwoven and elastic materials. The elastic inner layer 20 may also be formed from elastically stretchable film materials. One suitable elastic film is a breathable elastic film as described in U.S. patent application Ser. No. 10/703,761 filed on Nov. 7, 2003 and titled "Microporous Breathable Elastic Films, Methods of Making Same, And Limited Use or Disposable Product Applications", the disclosure of which is hereby incorporated by reference. Use of such breathable, elastic films may provide additional benefits for the skin health of the wearers of the garments of the invention. Other apertured elastic films may also be used as the inner layer 20.

Suitable elastic nonwoven materials include elastomeric materials that are treated using nonwoven manufacturing processes such as meltblowing. Suitable elastomers that may be formed into microfibers/nonwoven webs are described in U.S. Pat. No. 4,663,220 issued to Wisneski et al. on May 5, 1987 and titled "Polyolefin-Containing Extrudable Compositions and Methods for Their Formulation Into Elastomeric Products Including Microfibers", the disclosure of which is hereby incorporated by reference. Meltblowing of KRATON copolymers ("KRATON" is a trade designation of the Shell Chemical Company) to form composite nonwoven elastic webs is described in U.S. Pat. No. 4,657,802 issued to Morman on Apr. 14, 1987 and titled "Composite Nonwoven Elastic Web", the disclosure of which is hereby incorporated by reference.

The elastic inner layer 20 may also be formed from elastically stretchable laminate materials. U.S. Pat. No. 4,657,802 to Morman also describes composite nonwoven elastic webs, such as spunbond laminate (hereinafter "SBL") webs. Other elastically stretchable laminate materials include NBL materials as are described in U.S. Pat. No. 5,226,992 issued on Jul. 13, 1993 to Morman, the disclosure of which is hereby incorporated by reference. Additionally, suitable breathable elastic film laminates are described in Provisional U.S. patent application Ser. No. 60/518,100 filed on Nov. 7, 2003 and titled "Microporous Breathable Elastic Film Laminates, Methods of Making Same, and Limited Use or Disposable Product Applications", the disclosure of which is hereby incorporated by reference. Further, suitable elastic laminates are also described in a U.S. Patent Application (serial number not assigned) filed on Dec. 22, 2003 and titled "Extensible and Stretch Laminates and Method of Making Same", the disclosure of which is hereby incorporated by reference.

The elastic inner layer 20 is suitably compliant, soft feeling, and nonirritating to the wearer's skin, and may be liquid permeable or liquid impermeable. When the elastic inner layer 20 is liquid permeable, it may be sufficiently porous to permit liquid to readily penetrate through the thickness of the elastic inner layer 20. Desirably, the elastic inner layer 20 presents a relatively dry surface to the wearer of the disposable garment 100. In order for the elastic inner layer 20 to be liquid impermeable, the elastic inner layer 20 may be composed of a substantially hydrophobic material. The hydrophobic material may optionally be treated with a surfactant or otherwise processed to impart a desired level of wettability and hydrophilicity. The material used to form the elastic inner layer 20 may be surface treated with about 0.3 weight percent of a surfactant, such as a surfactant commercially available from Hodgson Textile Chemicals, Inc. under the trade designation AHCOVEL Base N-62. The surfactant may be applied by any conventional means, such as spraying, printing, brush coating or similar techniques. The surfactant may be applied to the entire elastic inner layer 20 or may be selectively applied to particular sections of the elastic inner layer 20, such as the medial section along the longitudinal centerline of the disposable garment 100, to provide greater wettability of such sections. The elastic inner layer 20 may further include a lotion or treatment applied thereto that is configured to be transferred to the wearer's skin. Suitable compositions for application to the elastic inner layer 20 are described in U.S. Pat. No. 6,149,934 that issued to Krzysik et al. on Nov. 21, 2000, the disclosure of which is hereby incorporated by reference.

The elastic inner layer 20 also has an elongate opening 90 formed therein in spaced relationship with the peripheral edges of the inner layer to facilitate lateral expansion of the inner layer during initial donning and during wear, and to allow bodily exudates to more readily pass through the inner layer to the absorbent assembly. The opening 90 may suitably be in the form of a slit or an aperture. The size of the opening 90 may be varied depending on the size of the disposable garment 100 and the intended functions of the elastic inner layer 20. The opening 90 may be described in terms of its length 95 relative to a total length 120 of the disposable garment 100 in the longitudinal direction 60 while the inner layer is in a generally relaxed (e.g., non-stretched) condition. The length dimension of the opening generally impacts the lateral expansion (e.g., laterally outward movement) and curvature of the side edges of the garment (e.g., at the leg openings thereof), with a greater length of the opening permitting increased lateral expansion of the side edges. As an example, the length 95 of the opening 90 may be from about 3% to about 90% of the total garment length 120. More suitably, the length 95 of the opening 90 may be from about 10% to about 90% of the total garment length 120, even more suitably from about 13% to about 70% of the total garment length, still more suitably from about 13% to about 63% of the total garment length, and still more suitably from about 25% to about 50% of the total garment length. Alternatively, the length 95 of the opening 90 may be from about 30% to about 50% of the total garment length 120. As a specific example of a suitable length for the opening 90, where the garment length 120 is about 381 millimeters (mm), the length 95 of the opening 90 may range from about 76 mm to about 267 mm. In addition to its length 95, the opening 90 may be characterized by its location within the elastic inner layer 20. The opening 90 may be disposed near the lateral centerline (the midpoint of the garment's width in the lateral direction) in the crotch region 50 of the garment 100. The opening 90 may extend in the longitudinal direction 60 toward the perimeters of the front waist region 30 and the back waist region 40.

The opening 90 is suitably disposed at least in part within the crotch region of the garment to facilitate the passage of body waste (e.g., urine and fecal matter) to the absorbent assembly 150. In the illustrated embodiment, the opening 90 is longitudinally centered in the crotch region of the garment 100 and extends longitudinally into the front waist region of the garment. Additionally, or alternatively, the opening 90 may extend from the crotch region into the back waist region of the garment 100. Extending the opening 90 into the front and/or back waist regions of the garment 100 allows for greater curvature of the garment at the leg openings (e.g., garment side edges) thereof upon lateral expansion of the garment.

If the opening 90 is in the form of a slit, the slit may be a single straight cut or a cut with branches. While not shown in the drawings, as an example of the latter the opening 90 may include a slit formed in the elastic inner layer 20 at the center of the garment 100 and may further include additional "branch" slits extending outward from the slit, particularly at the longitudinal ends thereof, in a direction other than the longitudinal direction of the slit. The opening 90 may also be in the form of an aperture. The aperture, unlike the slit, may form an open area in the elastic inner layer 20 through which the absorbent assembly 150 may be exposed. The aperture may be characterized by its open area in the relaxed (e.g., non-stretched) condition of the inner layer 20; for example, the open area of the aperture 90 may range from about 5% to about 25% of a total surface area of the elastic inner layer 20 in the relaxed condition thereof. More specifically, the open area of the aperture may range from about 7% to about 19% of the total surface area of the inner layer 20. Alternatively, the open area may be from 10% to about 14% of the total surface area of the inner layer 20.

In one specific example, the garment 100 may have a length 120 of about 381 mm, front and back waist region widths of about 241 mm and a crotch width of about 75 mm to provide a total surface area for the elastic inner layer 20 of about 3015 $mm^2$. The open area of the aperture 90 in such an example may range from about 101 $mm^2$ to about 508 $mm^2$. The aperture 90 may also be described in terms of its width. The maximum width of the aperture may range from about 13 mm to about 101 mm. More specifically, the width of the aperture 90 may range from about 25 mm to about 76 mm. The aperture may also be described in terms of its shape. For example, the elastic inner layer 20 may have an opening 90 in the shape of an hourglass, a rectangle, a trapezoid or other suitable shape.

Figure 2:
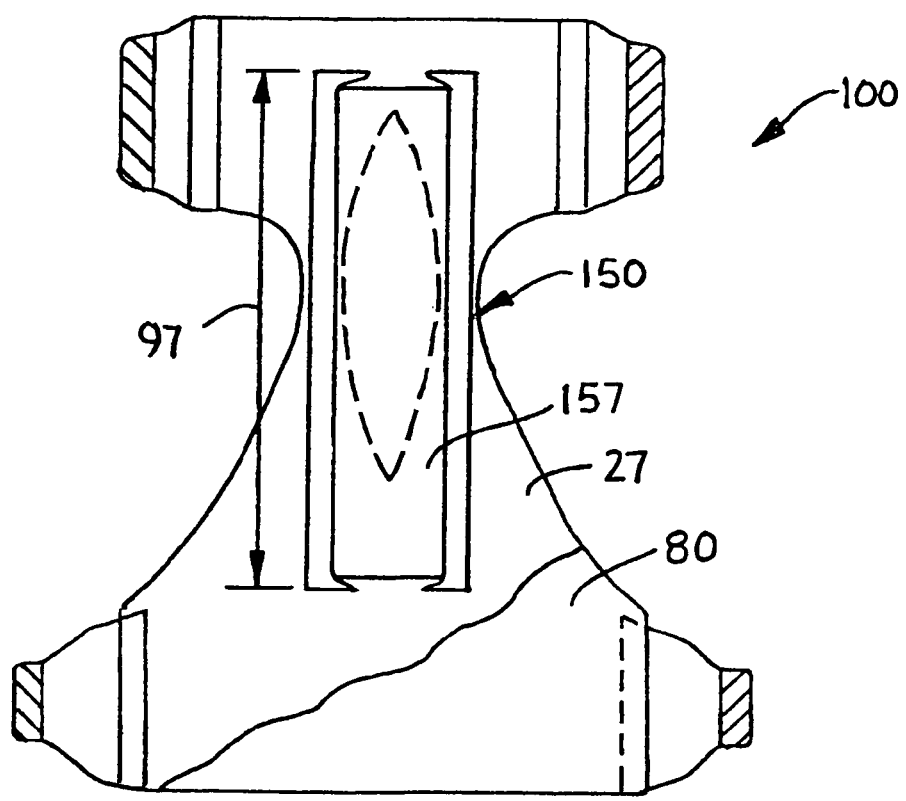
FIG. 2 representatively shows a plan view of the disposable absorbent garment of FIG. 1 with the exterior (or clothing-facing) surface of the garment facing the viewer.
Figure 6:
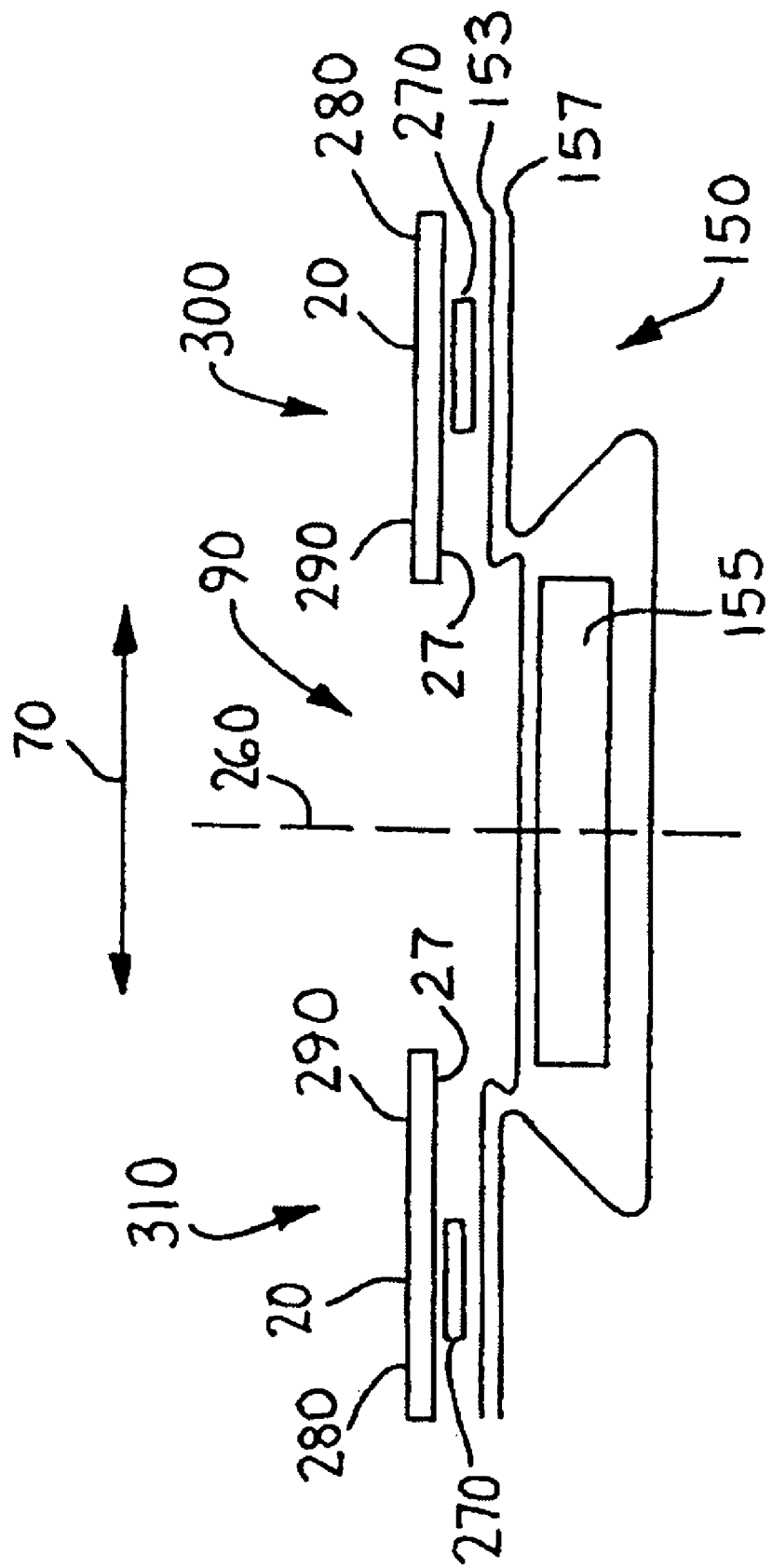
FIG. 6 representatively shows a cross-section of the crotch region of a disposable absorbent garment in which an absorbent assembly is attached by a "Z" fold.

With particular reference to FIG. 2, the absorbent assembly 150 is attached to the outer (e.g., exterior) surface 27 of the elastic inner layer 20 in generally overlapping relationship with the opening 90. Consequently, the absorbent assembly 150 holding the waste fluids is separated from the wearer's skin by the elastic inner layer 20. In the illustrated embodiment, the absorbent assembly 150 includes a topsheet layer 153, a core layer 155 and a barrier layer 157 (the topsheet layer 153, the core layer 155 and the barrier layer 157 are shown in FIG. 6). The topsheet layer 153 of the absorbent assembly 150 may define a bodyfacing surface that is compliant, soft feeling, and nonirritating to the wearer's skin. Further, the topsheet layer 153 may be less hydrophilic than the core layer 155. The topsheet layer 153 may be formed from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Various woven and nonwoven fabrics may be used for the topsheet layer 153. For example, the topsheet layer 153 may be formed of a meltblown or spunbond web of polyolefin fibers. The topsheet layer 153 may also be a bonded-carded web composed of natural and/or synthetic fibers. The topsheet layer 153 may be composed of a substantially hydrophobic material, and the hydrophobic material may, optionally, be treated with a surfactant or otherwise processed to impart a desired level of wettability and hydrophilicity. For example, the topsheet layer 153 may include a nonwoven, spunbond, polypropylene fabric composed of about 2.8-3.2 denier fibers formed into a web having a basis weight of about 22 grams per square meter and a density of about 0.06 gram per cubic centimeter.

The core layer 155 of the absorbent assembly 150 may suitably include a matrix of hydrophilic fibers, such as a web of cellulosic fluff, mixed with particles of a high-absorbency material commonly known as superabsorbent material. For example, the core layer 155 may include a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. Alternatively, the core layer 155 may include a laminate of fibrous webs and superabsorbent material or other suitable matrix for maintaining a superabsorbent material in a localized area. The size and the absorbent capacity of core layer 155 should be compatible with the size of the intended wearer and the liquid loading imparted by the intended use of the disposable absorbent garment 100. Further, the size and the absorbent capacity of the core layer 155 can be varied to accommodate wearers ranging from infants through adults.

The high-absorbency material may be selected from natural, synthetic, and modified natural polymers and materials. The high-absorbency materials may be inorganic materials, such as silica gels, or organic compounds, such as crosslinked polymers. The term "crosslinked" refers to methods for effectively rendering normally water-soluble materials substantially water insoluble but swellable. Such methods include, for example, physical entanglement, crystalline domains, covalent bonds, ionic complexes and associations, hydrophilic associations such as hydrogen bonding, and hydrophobic associations or Van der Waals forces. Examples of synthetic, polymeric, high-absorbency materials include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinyl morpholinone), poly(vinyl alcohol), and mixtures and copolymers thereof. Further polymers suitable for use in the core layer 155 include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and the like. Mixtures of natural and wholly or partially synthetic absorbent polymers may also be useful. The high absorbency material may be in any of a wide variety of geometric forms. As a general rule, the high absorbency material is in the form of discrete particles. However, the high absorbency material may also be in the form of fibers, flakes, rods, spheres, needles, or the like.

In general, the high absorbency material is present in the core layer 155 in an amount of from about 5 to about 90 percent by weight, desirably in an amount of at least about 30 percent by weight, and even more desirably in an amount of at least about 50 percent by weight based on a total weight of the core layer 155. For example, in a particular aspect, the core layer 155 may include a laminate which includes at least about 50 percent by weight and desirably at least about 70 percent by weight of high-absorbency material overwrapped by a fibrous web or other suitable material for maintaining the high-absorbency material in a localized area. An example of high-absorbency material suitable for use in the present invention is DRYTECH 2035 polymer available from Dow Chemical, a business having offices in Midland, Mich. Other suitable superabsorbents may include FAVOR SXM 880 polymer obtained from Stockhausen, a business having offices in Greensboro, N.C.

The barrier layer 157 may be formed from a thin plastic film or other flexible liquid-impermeable material. For example, the barrier layer 157 may be formed from a polyethylene film having a thickness of from about 0.013 millimeter (0.5 mil) to about 0.051 millimeter (2.0 mils). The barrier layer 157 may also be formed from a polyolefin film having a nonwoven web laminated to the exterior surface thereof, such as a spunbond web of polyolefin fibers. For example, a stretch-thinned polypropylene film having a thickness of about 0.015 millimeter (0.6 mil) may be thermally laminated thereto a spunbond web of polypropylene fibers. The polypropylene fibers may have a fiber diameter of about 15 to 20 microns, which nonwoven web has a basis weight of about 17 grams per square meter (0.5 ounce per square yard). The barrier layer 157 may include bicomponent fibers such as polyethylene/polypropylene bicomponent fibers. The barrier layer 157 may also include a vapor permeable non-woven facing layer laminated to a micro-porous film to impart "breathability" to the barrier layer. Suitable "breathable" barrier layer 157 materials are described in U.S. Pat. No. 5,695,868 issued Dec. 9, 1997 to McCormack et al. and U.S. Pat. No. 5,843,056 issued Dec. 1, 1998 to Good et al., the descriptions of which are hereby incorporated by reference.

As shown in FIG. 6, the topsheet layer 153 and the barrier layer 157 may extend laterally beyond the longitudinal side edges of the core layer 155. The lateral extensions of the topsheet layer 153 and the barrier layer 157 may be C-folded or Z-folded prior to attachment to the exterior surface 27 of the elastic inner layer 20. FIG. 6 shows the lateral extensions of the topsheet layer 153 and the barrier layer 157 being Z-folded and attached to the exterior surface 27. The attachment regions 270 may be formed by adhesive, ultrasonic or thermal bonds. The lateral extensions of the topsheet layer 153 and the barrier layer 157 provide additional volume to hold a larger quantity of absorbent and waste materials without affecting the fit of the garment 100. Moreover, because the lateral extensions of the absorbent assembly 150 are attached to the exterior surface of the inner layer 20, upon lateral elongation of the inner layer due to an elongation force, such as due to movements of the wearer, the absorbent assembly expands laterally while still overlapping the expanded opening 90 of the inner layer. Suitably, the elastic inner layer 20 is elongated between about 5% to about 50% before the absorbent assembly 150 is attached thereto. More suitably, the elastic inner layer 20 is elongated between about 10% to about 30% prior to attachment, and even more suitably between about 15% and about 20%.

The absorbent assembly 150 may be constructed in such a way that when it is attached to the elastic inner layer 20, leg cuffs 280 and containment flaps 290 are formed. The leg cuffs 280 may be formed by the portions of the elastic inner layer 20 that extend laterally outward from the attachment regions 270. The containment flaps 290 may be formed by the portions of the elastic inner layer 20 that extend laterally inward from the attachment region 270. The presence of the opening 90 approximately divides the elastic inner layer 20 into two halves around a front body line 260 of the garment 100. The elastic inner layer 20 may be divided into a right inner elastic layer region 300 and a left inner elastic layer region 310. The absorbent assembly is shown as being attached to the right inner elastic layer region 300 and the left inner elastic layer region 310 by the attachment regions 270. The attachment regions 270 may run the full length 97 of the absorbent assembly 150 (length 97 is shown in FIG. 2). Desirably, the attachment regions 270 are located approximately in the centers of the right inner elastic layer region 300 and the left inner elastic layer region 310. This positioning of the attachment regions 270 permits the formation of the leg cuffs 280 and the containment flaps 290. For each inner elastic layer region, it is desirable for about 10% of the elastic inner layer 20 to extend laterally outward from the attachment region 270 to form a leg cuff 280 and about 90% of the elastic inner layer 20 to extend laterally inward from the attachment region 270 to form a containment flap 290. More desirably, about 30% extends outward to form a leg cuff 280 and about 70% extends inward to form a containment flap 290 and even more desirably, about 50% extends outward to form a leg cuff 280 and about 50% extends inward to form a containment flap 290.

The lateral width of the attachment regions 270 may range from about 2 mm ("mm"=millimeters) to about 60 mm. More desirably, the width of the attachment regions 270 may be from about 3 mm to about 40 mm and even more desirably, from about 4 mm to about 20 mm. While the attachment regions 270 may extend the full length 97 of the absorbent assembly 150, it may desirable for the attachment regions 270 to have a length of from about 100 mm to about 390 mm, depending on the size of the absorbent assembly 150 and the overall size of the garment 100. More desirably, the attachment regions 270 have a length of from about 150 mm to about 350 mm and even more desirably, a length of from about 200 mm to about 300 mm. The length 97 of the absorbent assembly 150 is desirably selected so that the entire length 95 of the opening 90 is covered (e.g., underlied) by the absorbent assembly 150 when the absorbent assembly is attached to the exterior surface 27 of the elastic inner layer 20. In addition to the attachment regions 270 shown in FIG. 6, the lateral edges of the absorbent assembly 150 may be selectively attached to the exterior surface 27 of the elastic inner layer 20 in order to provide a seal that prevents leakage of wastes being contained by the absorbent assembly 150.

Figure 6A:
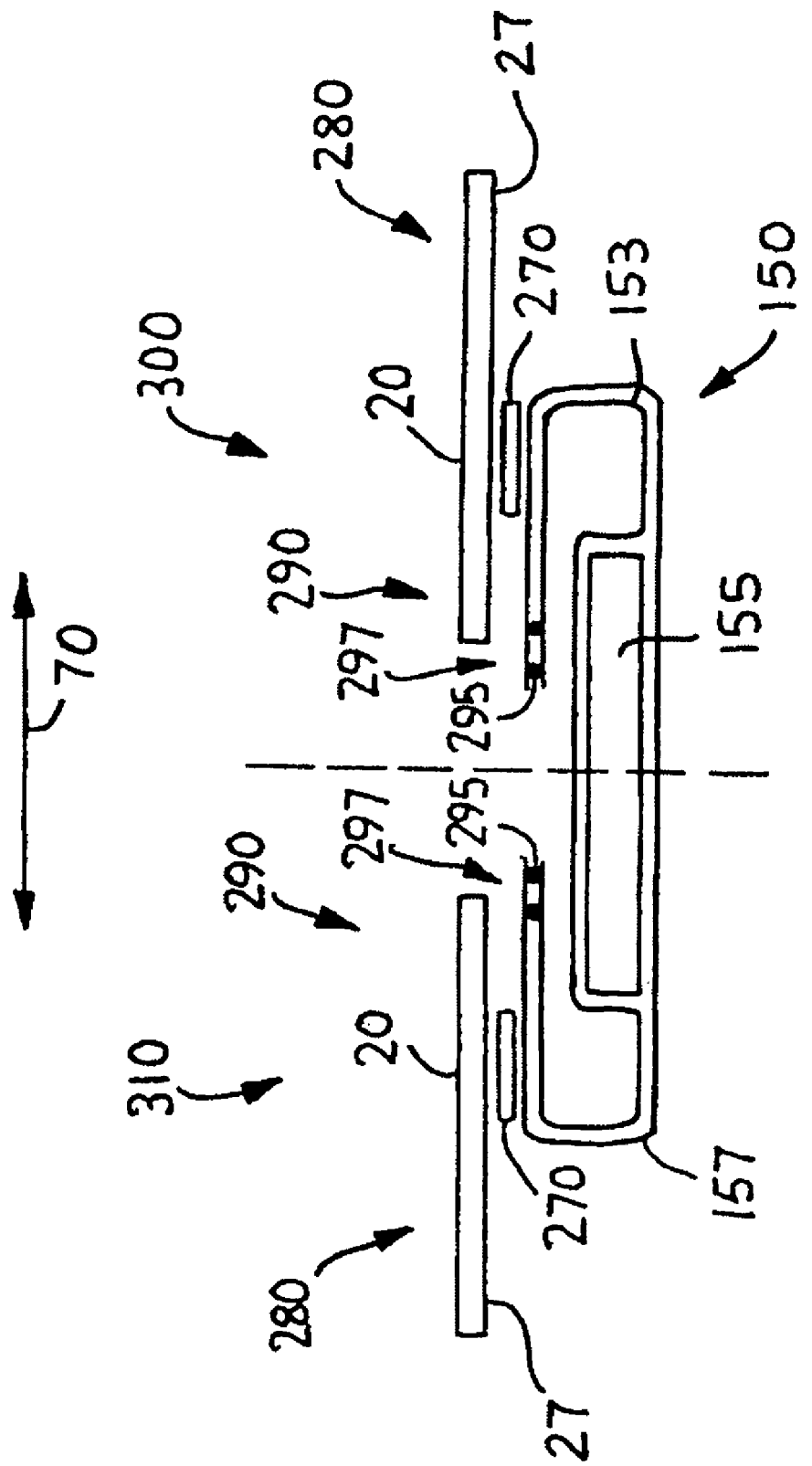
FIG. 6A representatively shows a cross-section through a crotch region of a disposable absorbent garment invention in which an absorbent assembly is attached by a "C" fold.

In a further aspect of the present invention, leg cuffs and barrier cuffs may alternatively be formed by lateral extensions of the topsheet layer 153 and the barrier layer 157. For example, in FIG. 6, where the absorbent assembly 150 is Z-folded and attached to the exterior surface 27 of the elastic inner layer 20, the portions of the topsheet layer 153 and the barrier layer 157 that extend laterally beyond the attachment regions 270 may extend further outward in the lateral direction 70. Elastic elements may be attached to the lateral extension of the topsheet layer 153 or attached in between the lateral extensions of the topsheet layer 153 and the barrier layer 157 to form leg cuffs and containment flaps. The longitudinal side edges of the topsheet layer 153 and the barrier layer 157 may be gathered by the elastic elements to form the leg cuffs. FIG. 6A representatively illustrates how the absorbent assembly 150 may be C-folded and attached to the exterior surface 27 of the elastic inner layer 20. With the aspect depicted in FIG. 6A, the barrier layer 157 is directly attached to the exterior surface 27 of the elastic inner layer 20 at the attachment regions 270. With the C-fold shown in FIG. 6A, the topsheet layer 153 and the barrier layer 157 may not be extended laterally outward to form leg cuffs and containment flaps. However, elastic elements 295 may be attached in between the C-fold ends of the topsheet layer 153 and the barrier layer 157 to form secondary flaps 297. The secondary flaps 297 provide additional containment of wastes within the absorbent assembly 150. The elastic elements 295 may be formed by elastic strands or elastic films.

Figure 3:
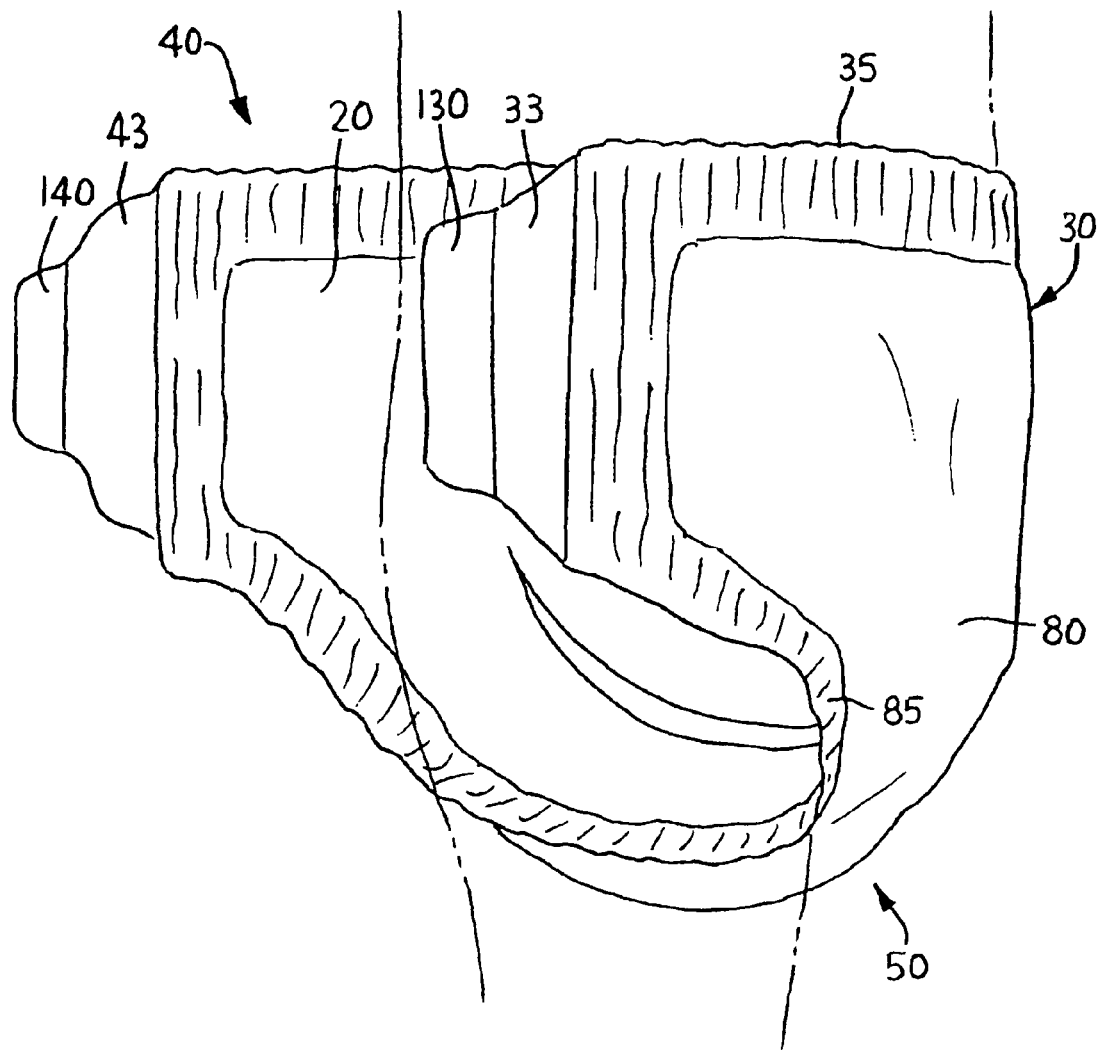
FIG. 3 representatively shows a perspective view of the disposable absorbent garment of FIG. 1 as it would be applied to a wearer (prior to fasteners being attached); the disposable absorbent garment also includes an outer layer in this figure.
Figure 4:
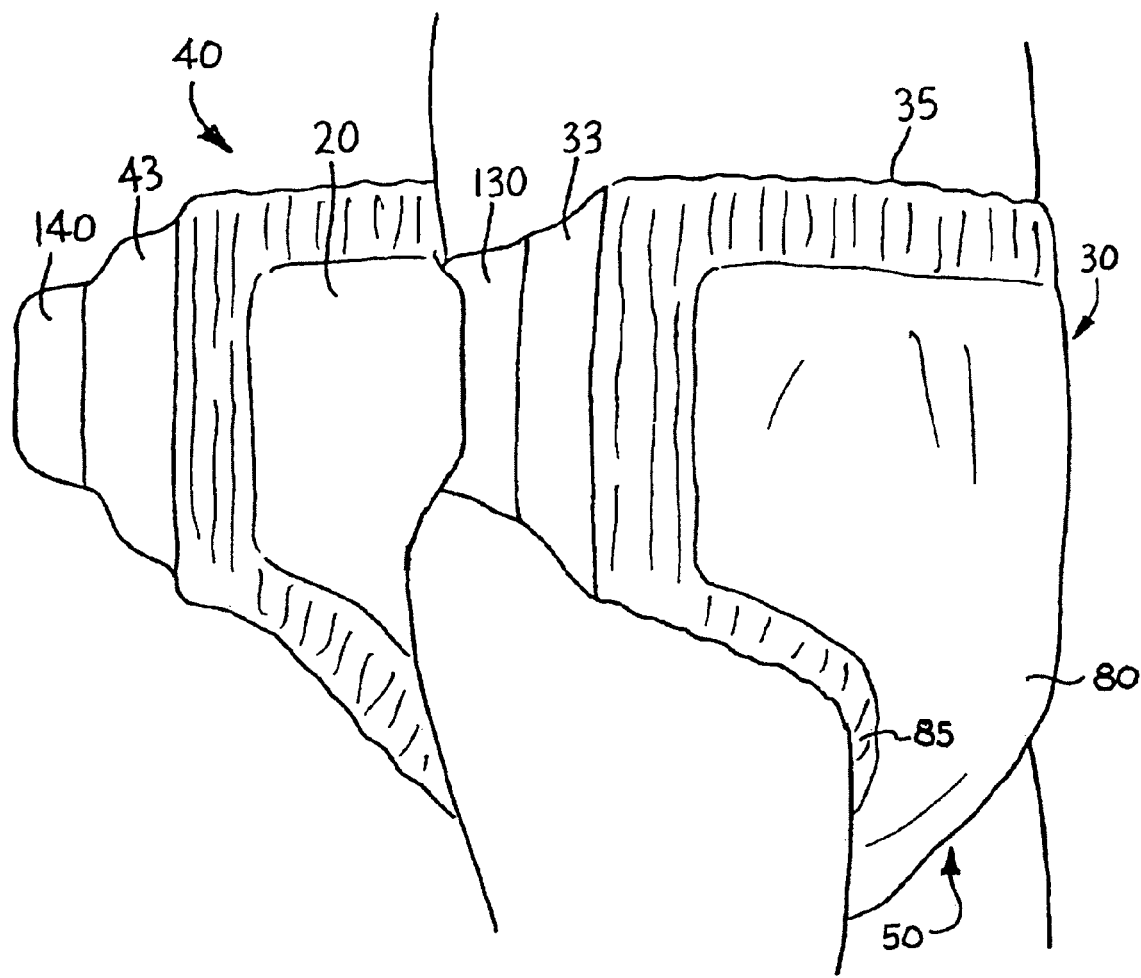
FIG. 4 representatively shows a perspective view of the disposable absorbent garment of FIG. 3 with a fastener being attached to the elastic inner layer.
Figure 5:
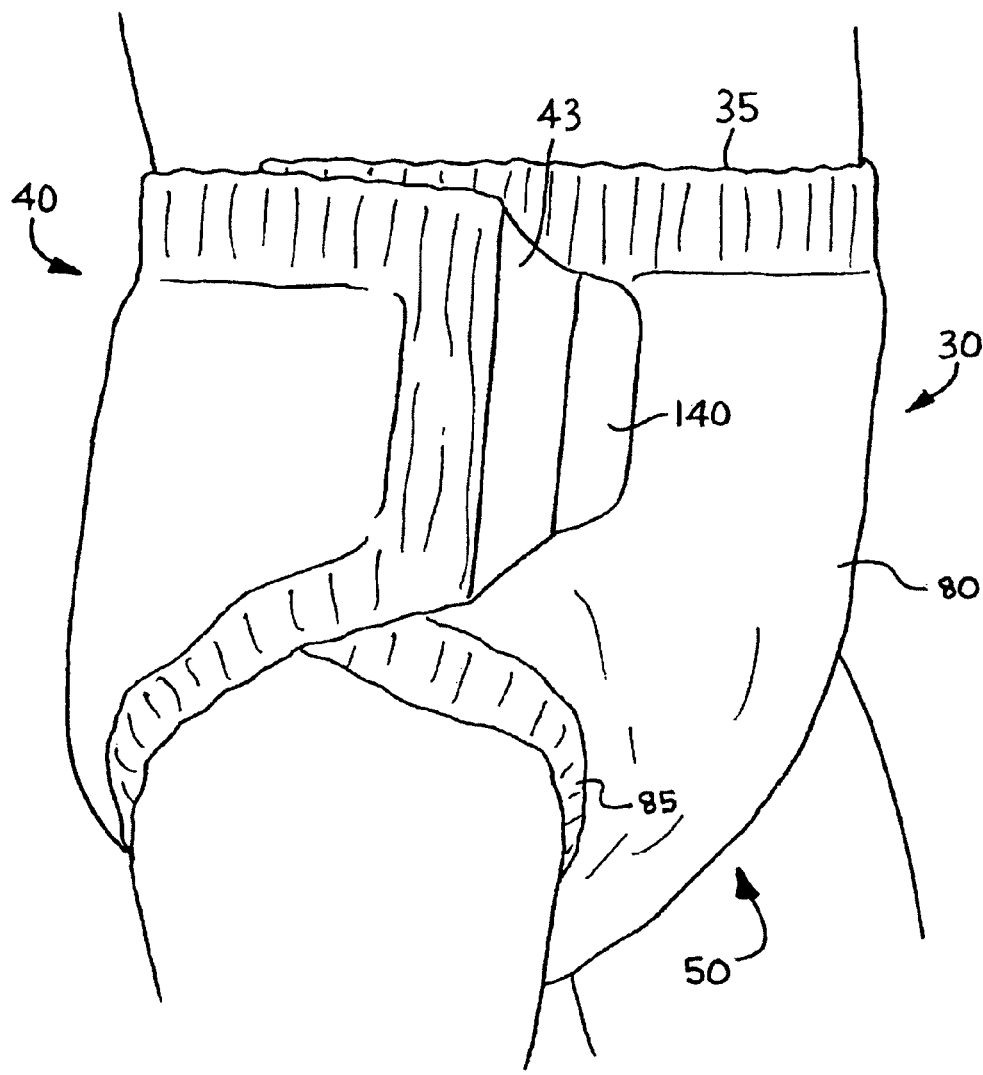
FIG. 5 representatively shows a perspective view of the disposable absorbent garment of FIG. 3 with a fastener being attached to the outer layer.

The disposable absorbent garment 100 may further include mechanical fasteners 130 and 140 for attaching the front waist region 30 and the back waist region 40 together. The material forming the mechanical fasteners 130 and 140 may be integral with the elastic inner layer 20 (and the outer layer 80 when the garment 100 includes an outer layer 80) or the material may be provided on separate portions (e.g. front ear portion 33 and back ear portion 43) that are attached to the longitudinal side edges 55 of the garments 100 in the waist regions. In FIGS. 1-5, the mechanical-fasteners 130 and 140 are provided on separate portions that are attached to the garment 100 near the longitudinal side edges 55. The mechanical fasteners 130 and 140 may include a variety of materials and surfaces known for mechanical engagement such as buttons, pins, snaps, adhesive tape fasteners, cohesives, mushroom-and-loop fasteners and hook and loop fasteners. FIGS. 3-5 representatively illustrate how the mechanical fasteners 130 and 140 may be positioned to join the front waist region 30 and the back waist region 40. The garment 100 illustrated in FIGS. 3-5 includes an outer layer 80 (the outer layer 80 will be described in more detail herein). FIG. 3 illustrates the appearance of the mechanical fasteners 130 and 140 prior to engagement; FIG. 4 illustrates the engagement of mechanical fastener 130 into the elastic inner layer 20 of the garment 100 in the back waist region 40; and FIG. 5 illustrates how mechanical fastener 140 may be brought in overlapping relationship with mechanical fastener 130 for engagement into the outer layer 80 of the garment 100 in the front waist region 30.

Most commercially-available diapers include a fastener attached to the back waist region in such a way that the fastener may engage the front waist region of the diaper. This type of fastening system may result in the front waist region drooping or sagging during wear. The combination of mechanical fasteners 130 and 140 and how they are integrated with the overall design of the disposable absorbent garments 100 of the invention prevents such a loss of fit. As will be described in more detail herein, the front waist region fastener 130 is positioned on the longitudinal side edge 55 of the garment 100 in such a way so as to be capable of extending beyond the garment seam line 160 (FIG. 12) to engage the elastic inner layer 20. The garment seam line 160 is located behind the center line of the side of the wearer. By positioning the front waist region fastener 130 beyond the garment side seam line 160, the fastener 130 is moved out of the highly compressed area in the front waist region 30 of the garment 100. There are at least five features of the location of the front waist region fastener 130 that affect the quality of garment fit and fastener engagement during wear: (1) distance of the front waist region fastener 130 from an "extended crotch line" 170; (2) the angle "α" (FIG. 13) of the crotch line 170 at the narrowest crotch width 57 to the bottom of the front waist region fastener 130; (3) the narrowest crotch width 57 (distance from one leg edge to the other at the narrowest portion of the crotch region 50); (4) the front center panel length 190 (distance from the narrowest crotch width 57 to the front waist edge 35 of the garment 100); and (5) the front waist region fastener length 200. These features are representatively illustrated in FIG. 13.

Figure 12:
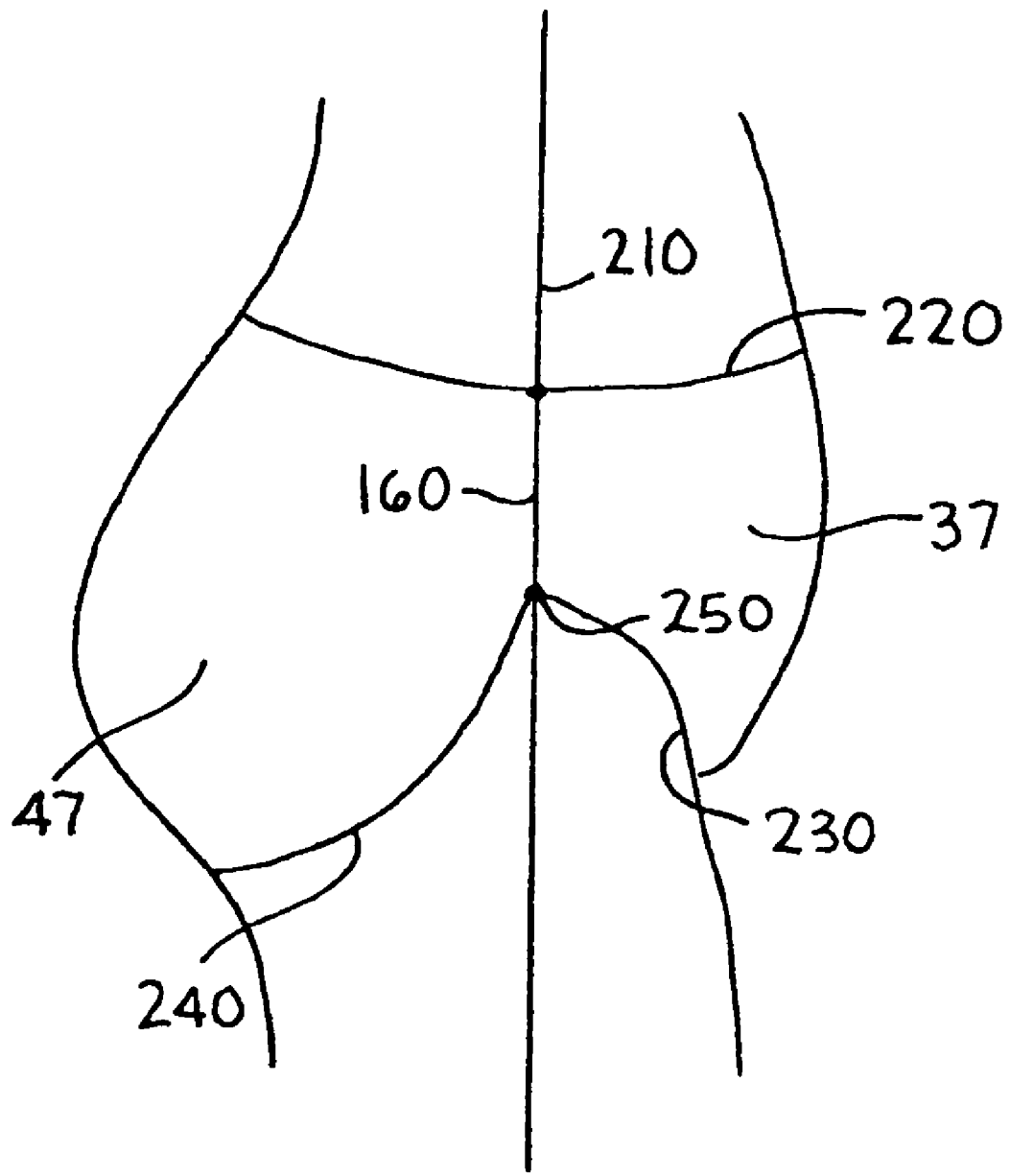
FIG. 12 representatively shows a side view of a child's torso at the waist, hip and thigh.

FIG. 12 representatively illustrates a side view of a child's torso at the waist, hip and thigh. An imaginary side center line 210 is positioned in the center of the side view. The side center line 210 bisects the side and creates a front side 37 and a back side 47. A waist line 220 that is generally perpendicular to the side center line 210 is also shown. A back leg line 240 comes up from the back of the crotch, below the buttocks and then comes almost straight up to the waist line 220. A front leg line 230 originates at the front of the crotch, comes up and extends toward the side center line 210. The bottom 250 of the garment side seam 160 is formed where the front leg line 230 crosses the back leg line 240. The garment side seam 160 is represented by a line parallel to the side center line 210 from the waist line 220 down to the bottom 250 of the garment side seam 160. The garment side seam 160 defines an ideal location for the best leg and waist fit in the front and back of a disposable garment 100. Desirably, the front waist region fastener 130 engages the elastic inner layer 20 at a location that is on the back side 47 of the garment side seam 160. Put differently, when the front waist region fastener 130 is engaged into the elastic inner layer 20 in back of the garment side seam 160, the location of the front waist region fastener 130 is greater than the distance 180 of the front waist region fastener 130 from a front body line 260. A representation of the front body line 260 and the distance 180 of a front waist region fastener 130 from the front body line 260 is shown in FIG. 13.

Figure 13:
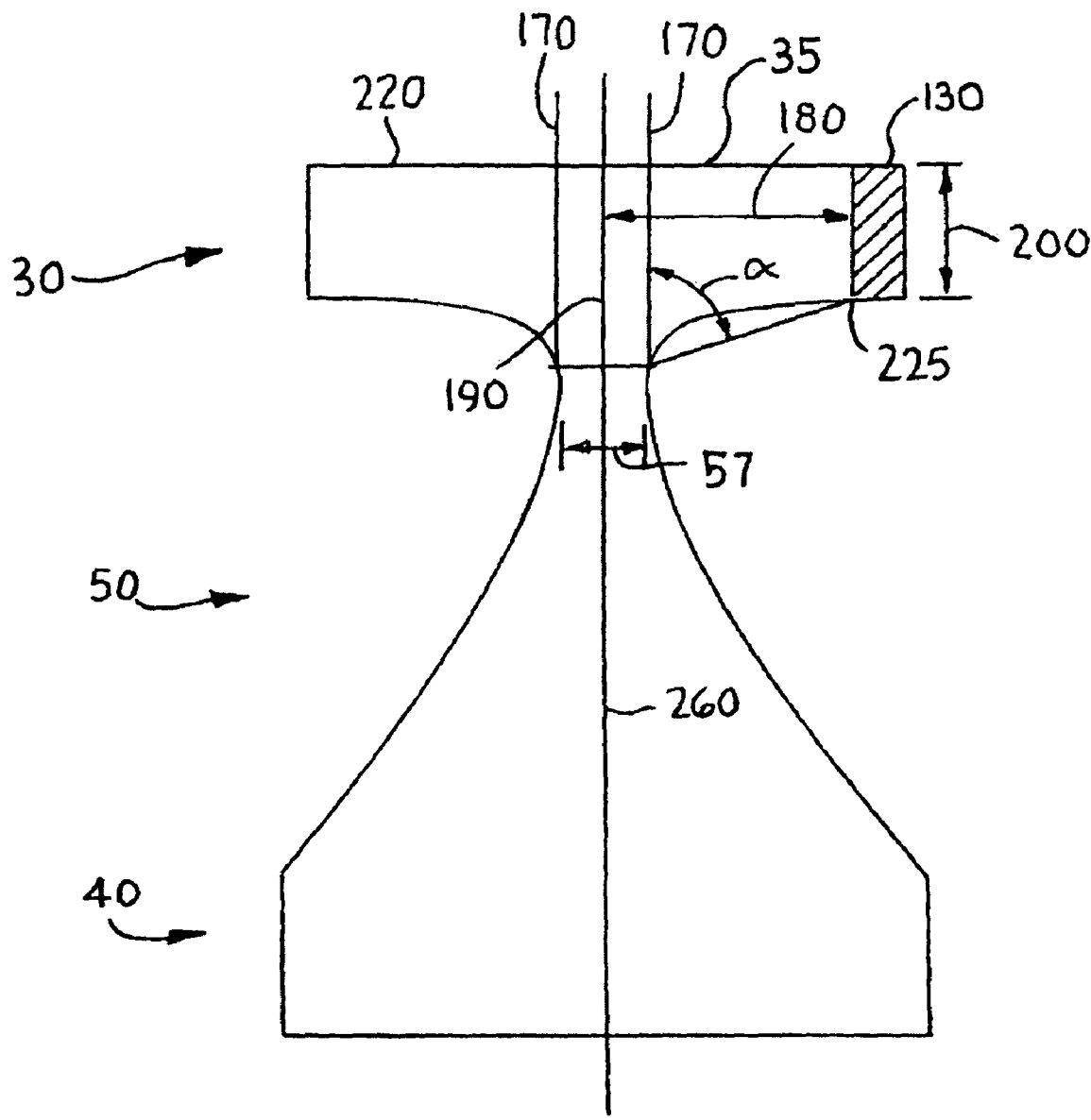
FIG. 13 representatively shows a plan view of the body lines of the wearer of a disposable garment.

FIG. 13 representatively illustrates a plan view of the body lines of a young child. The body lines form an outline that generally corresponds to the regions of a disposable absorbent garment: a front waist region 30, a back waist region 40 and a crotch region 50. A front body line 260 is shown that bisects the length of the outline of body lines. The location of the width 57 at the narrowest portion of the crotch region 50 is identified. Two imaginary crotch lines 170 are shown and are parallel to the front body line 260. The significant portion of the crotch lines 170 is the portion between the width 57 at the narrowest portion of the crotch and the front waist line 220. While FIG. 13 shows the outline of body lines, an example of a front waist region fastener 130 may be shown within the outline in order to illustrate the significance of the imaginary angle "α" that may be drawn between the crotch line 170 and the location of the bottom 225 of the front waist region fastener 130. Desirably, the crotch-to-fastener angle α from the crotch line to the bottom 225 of the front waist region fastener 130 is greater than about 45 degrees. Even more desirably, the crotch-to-fastener angle α is greater than about 65 degrees. Even though the bottom 225 of the front waist region fastener 130 is not drawn in such a way to result in a crotch-to-fastener angle α of 90 degrees, an angle α of 90 degrees is very desirable. The relationship between the crotch line 170 formed based on the location of the width 57 at the narrowest portion and the location of the front waist region fastener 130 (which may be defined by the location of the bottom 225) impacts the quality of fit and the duration of a high quality of fit provided by the disposable garments 100 of the invention.

The width 57 at the narrowest portion of the crotch region 50 also impacts garment fit and fastener engagement. For example, as the width 57 at the narrowest portion is increased, the crotch-to-fastener angle α from the crotch line 170 to the bottom 225 of the front waist region fastener 130 decreases. Therefore, it is desirable that the disposable absorbent garments of the invention have a width 57 at the narrowest portion of equal to or less than about 4 inches (101 mm). A width 57 at the narrowest portion of equal to or less than 3.5 inches (89 mm) is more desirable and a width 57 at the narrowest portion of equal to or less than 3.0 inches (76 mm) is even more desirable. The narrow width 57 is desirable regardless of the size of the intended wearer of the disposable absorbent garment 100. That is, a disposable absorbent garment 100 having a width 57 at the narrowest portion of 3.0 inches (76 mm) will provide sufficient coverage regardless of whether the wearer of the garment 100 is an infant or an adult. Another feature that impacts garment fit and the quality of fastener engagement is the front center panel length 190. Although the front center panel length 190 illustrated in FIG. 13 is shown on an outline of body lines, the same dimension could be determined on an actual disposable absorbent garment. The front center panel length 190 may be described as the distance from the width 57 at the narrowest portion of the crotch region 50 to the front waist line 220. As the front center panel length 190 gets longer, the crotch-to-fastener angle α to the bottom 225 of the front waist region fastener 130 gets smaller. Therefore, it is desirable that the disposable absorbent garments of the invention have a front center panel length 190 of about 6 inches (152 mm) or less. A front center panel length 190 of 5 inches 127 mm) or less is more desirable and a front center panel length 190 of 4.5 inches (114 mm) or less is even more desirable.

Another feature of the location of the front waist region fastener 130 that may impact garment 100 fit and fastener engagement is the length 200 of the front waist region fastener 130. When the length 200 of the front waist region fastener 130 is decreased, the crotch-to-fastener angle α decreases. Therefore, it is desirable that the length 200 of the front waist region fastener 130 be equal to or less than the front center panel length 190. More desirably, the length 200 of the front waist region fastener 130 is equal to or less than 75% of the front center panel length 190. Even more desirably, the length 200 of the front waist region fastener 130 is equal to or less than 50% of the front center panel length 190. Various combinations of the features related to the position of the front waist region fastener 130 may be identified to improve the overall fit and fastener engagement of the disposable garments 100 of the invention.

In order to provide a unitary feel and appearance, the garments 100 of the invention may further comprise an outer layer 80 that overlays the absorbent assembly 150 and the exterior surface 27 of the elastic inner layer 20. The outer layer 80 (visible in FIG. 2) may be formed of a stretchable material such that the outer layer 80 is extensible or elastic. When the outer layer 80 is formed of an extensible material, the outer layer 80 is capable of extending in the longitudinal direction 60, the lateral direction 70 or both the longitudinal direction 60 and the lateral direction 70. As will be described in further detail herein, extensible materials are capable of stretching but do not substantially return to their original length when the pulling force is removed. Instead, extensible materials experience some degree of permanent elongation from their original length. As with the elastic inner layer 20, when the outer layer 80 is formed of an elastic material, the outer layer 80 is capable of elastically stretching in the longitudinal direction 60, the lateral direction 70 or both the longitudinal direction 60 and the lateral direction 70. When it is desirable for the outer layer 80 to include an elastic material, suitable elastic materials may be selected from those described herein as being suitable for the inner elastic layer 20.

Just as the size of the opening 90 may be related to the elastic inner layer 20 in terms of surface area, the size of the elastic inner layer 20 relative to the outer layer 80 may be considered in terms of surface area. For example, the elastic inner layer 20 may have a smaller surface area than the outer layer 80. As surface area is determined by length and width, the outer layer 80 may have a greater length in the longitudinal direction 60 of the disposable garment 100 than the elastic inner layer 20. The length of the elastic inner layer 20 may be determined when the elastic inner layer 20 is in a relaxed and retracted state. The outer layer 80 may also have a width in the lateral direction 70 that is greater than the width of the elastic inner layer 20 in the lateral direction 70. When the garment 100 is constructed so that the elastic inner layer 20 is smaller than the outer layer 80 in its relaxed, retracted state, the elastic inner layer 20 provides a snug fit against the body of the wearer of the garment 100 while the larger, outer layer 80 provides area and volume for containment.

There are several approaches for providing a garment 100 having an elastic inner layer 20 that is smaller than the outer layer 80. For example, the elastic inner layer 20 may be stretched or elongated during manufacture and then attached to an outer layer 80 formed of non-stretchable material. The layers may be attached to each other using known bonding techniques such as adhesive, ultrasonic or thermal bonding. The elastic inner layer perimeter 25 may be attached to the outer layer 80. The elastic inner layer perimeter 25 may be "matched" up with the outer layer perimeter or the elastic inner layer perimeter 25 may be attached to the outer layer 80 within the outer layer perimeter. After the elastic inner layer 20 and the outer layer 80 are bonded together, the elongated elastic inner layer 20 retracts and gathers the outer layer 80. As a result, the gathered outer layer 80 may appear blousy.

Figure 7:
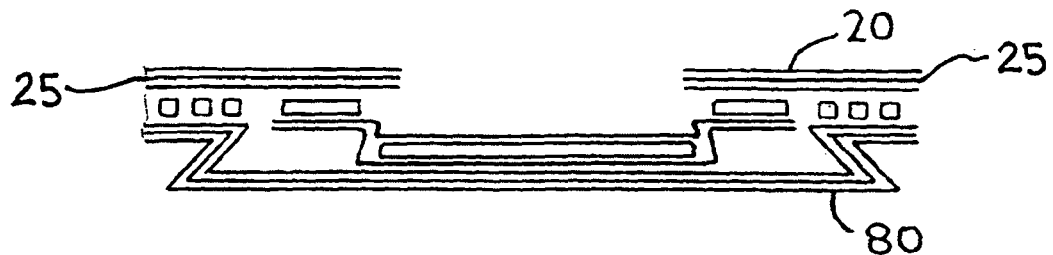
FIG. 7 representatively shows a cross-section of the crotch region of a disposable absorbent garment such as the one shown in FIG. 2, where the garment also includes an outer layer having a larger size than the elastic inner layer.
Figure 8:
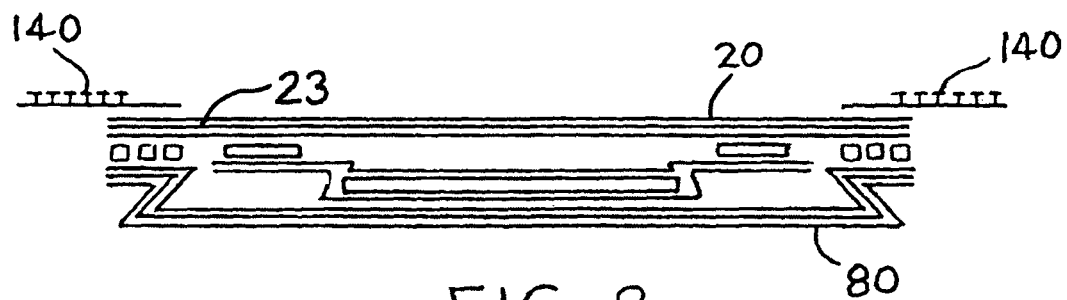
FIG. 8 representatively shows a cross-section of the back waist region of a disposable garment such as the one shown in FIG. 7.

FIG. 7 representatively shows a cross-section of the crotch region 50 of the garment 100 shown in FIG. 2 after an elastic inner layer 20 was elongated, the elastic inner layer perimeter 25 was bonded to the outer layer perimeter and the garment 100 was allowed to relax. FIG. 7 shows the gathered outer layer 80 having a greater width than the elastic inner layer 20. FIG. 8 representatively shows a cross-section of the back waist region 40 of the garment 100 shown in FIG. 1 in which fasteners 140 are provided near the longitudinal side edge 55 of the elastic inner layer 20. The fasteners 140 may be used to join the back waist region 40 with the front waist region 30 when the garment 100 is donned. The fasteners 140 may be provided on the interior surface 23 of the elastic inner layer 20. As described herein, interior surface 23 is the surface of the elastic inner layer 20 that comes into contact with the wearer's skin. The fasteners 140 may be provided near the longitudinal side edge 55 of the garment 100 and near where the elastic inner layer perimeter 25 is bonded to the outer layer 80. Positioning the fasteners 140 in this location provides for the smaller elastic inner layer 20 to stretch before the outer layer 80 during application and as a result, the elastic inner layer 20 may snuggly fit to the body.

As described herein, the elastic inner layer 20 may be provided by a material that has multi-directional stretch. When the elastic inner layer 20 is stretched in more than one direction prior to bonding with the outer layer 80, the resulting garment 100 has an outer layer 80 that has been gathered in more than one direction. A gathered perimeter may be formed by the elongated elastic inner layer 20 being bonded to the non-stretchable outer layer 80. This construction provides the advantage of an outer layer 80 that may be gathered in any shape or surface area needed for a particular disposable garment design. This construction also provides the ability to form a garment 100 having areas of curvature (e.g. highly curved gatherings) without the need to incorporate individual, highly-curved elastic components.

The degree to which the outer layer 80 is gathered is related to the elongation and stretch direction of the elastic inner layer 20. When the elastic inner layer perimeter 25 is bonded to the outer layer 80, the direction of stretch of the elastic inner layer 20 will create gathers. The elastic inner layer 20 may be constructed of elastic materials that are capable of providing a range of tension and percent elongation. For example, the material may have a percent elongation of from about 10% to about 400%. More specifically, the percent elongation may range from about 30% to about 200% or from about 50% to about 150%. The percent elongation may be different in different directions of stretch. For example, a suitable elastic material for constructing the elastic inner layer 20 may have a percent elongation of 50% in the cross-direction (or lateral direction 70) and a percent elongation of 100% in the machine direction (or longitudinal direction 60). Suitable elastic materials may also be characterized by the force to elongate the material and the retractive force that the material provides during use. For example, the force to elongate may range from about 100 grams to about 1000 grams (based on elongating a 7.62 centimeter (cm) wide sample to 50% elongation). More specifically, the force to elongate may range from about 200 grams to about 800 grams or from about 400 grams to about 600 grams. The retractive force provided during use may be similar to the force to elongate. These forces to elongate and forces to retract of the elastic inner layer 20 are suitable whether the garment 100 includes an outer layer 80 or not.

Figure 9:
FIG. 9 representatively shows a cross-section of the crotch region of a disposable absorbent garment such as the one shown in FIG. 2 before the garment is donned and including an outer layer that is formed from an extensible material.
Figure 10:
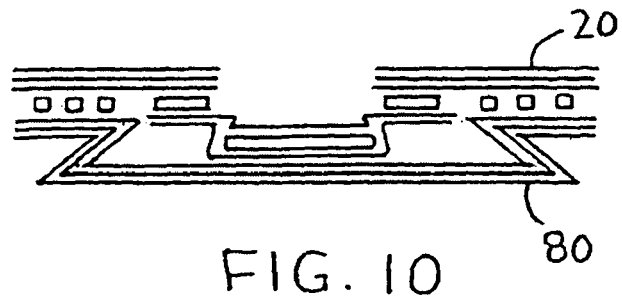
FIG. 10 representatively shows a cross-section of the crotch region of a disposable absorbent garment such as the one shown in FIG. 9 after the garment is donned.

Another approach for providing a garment 100 having an elastic inner layer 20 that is smaller than the outer layer 80 is to provide an outer layer 80 formed from an extensible material. The extensible material may be capable of extending in a machine direction (e.g. longitudinal direction 60) and/or a cross-direction (e.g. lateral direction 70). Extensible materials are capable of increasing their length in a given direction and therefore, their area, with minimal force. The percent extensibility of a material may be defined as the difference between the extended surface area and the initial surface area divided by the initial surface area; the quotient then being multiplied by 100. With a multi-directional extensible material, the material may increase its length in multiple directions and therefore, increase the surface area of the outer layer 80 to a degree related to the percent extensibility of the material. For example, the percent extensibility of a suitable material may range from about 10% to about 150%. More specifically, the percent extensibility may range from about 20% to about 80% or from about 30% to about 50%. Suitable materials for forming an extensible outer layer 80 are described in U.S. Pat. No. 6,610,383 entitled "Transversely Extensible and Retractable Necked Laminate of Non-Elastic Sheet Layers" which issued on Aug. 26, 2003 to Morman et al. and U.S. Pat. No. 6,632,212 entitled "Breathable Laminate Permanently Conformable to the Contours of A Wearer" which issued on Oct. 14, 2003 to Morman et al., the disclosures of which are hereby incorporated by reference. An advantage of this approach is that the elastic inner layer 20 does not have to be elongated prior to bonding to the outer layer 80. Another difference is that bonded region may not have a gathered appearance prior to the garment 100 being worn. When the garment 100 is stretched during donning, the outer layer 80 formed with an extensible material will elongate, thereby increasing its area and creating a gathered appearance where the elastic inner layer perimeter 25 is bonded. This aspect is representatively illustrated in FIG. 9 and FIG. 10. FIG. 9 representatively shows a cross-section of a disposable garment 100 such as that shown in FIG. 1 in which the outer layer 80 is formed from an extensible material, prior to the garment 100 being donned. In FIG. 9, the length of the outer layer 80 is the same as the length of the elastic inner layer 20. FIG. 10 representatively shows the same cross-section as FIG. 9, but after the garment 100 has been stretched, such as during donning. In FIG. 10, the length of the outer layer 80 is greater than the length of the elastic inner layer 20.

Yet another approach to providing a garment 100 having an elastic inner layer 20 that is smaller than the outer layer 80 is to use an outer layer 80 that has a three-dimensional shape. As with the previous approach, an advantage of this approach is that the elastic inner layer 20 does not have to be elongated prior to bonding with the outer layer 80. An example of an outer layer 80 having a three-dimensional shape is to provide an outer layer 80 that has one or more pleats. The pleats permit an outer layer 80 having a length that is greater than the length of an attached elastic inner layer 20 in the cross-direction of the garment 100. While these approaches may be used to provide an outer layer 80 having a greater area than the relaxed area of the elastic inner layer 20, the garments 100 of the invention may also include an outer layer 80 that does not completely overlay the entire area of the elastic inner layer 20. For example, the outer layer 80 may only overlay the absorbent assembly 150.

As already described herein, the disposable garments 100 of the invention may be constructed in such a way that the elastic inner layer perimeter 25 is bonded to the outer layer 80. The elastic inner layer perimeter 25 may be bonded by using bonding techniques such as adhesive, ultrasonic or thermal bonds. In one aspect, the elastic inner layer perimeter 25 is bonded to the perimeter of the outer layer. The perimeter bonding of the components permits the elastic inner layer 20 to fully stretch. Additionally, as already described, when the elastic inner layer 20 is bonded to an outer layer 80 formed of a non-stretchable material, the perimeter bonding creates the visual appearance of gathered waist and leg regions without the addition of separate elastic components, such as waistbands and leg elastics. Elimination of the need to incorporate separate elastic components results in a garment 100 that lies flat. This feature is significant when the garment 100 is in the form of an infant diaper; diapers that lie flat are easier to apply to infants and toddlers than diapers that want to curl closed. Additionally, the perimeter bonding provides an elastic inner layer retraction value that is greater than an outer layer retraction value. Desirably, the elastic inner layer retraction value is greater than the outer layer retraction value regardless of the type of material from which the outer layer 80 is made. If the outer layer 80 is made from a non-stretchable material, the elastic inner layer retraction value will be inherently greater (because the material of the outer layer 80 has no significant retraction). If the outer layer 80 is made from an extensible material or an elastic material, the retractive force of that material is desirably less than the retractive force of the material used to form the elastic inner layer 20.

The perimeter bonding that is used to form garments 100 of the invention may have several characteristics. For example, one characteristic is the percent of the perimeter of the elastic inner layer 20 that is bonded to the outer layer 80. In FIGS. 3-5, 100% of the elastic inner layer perimeter is shown as being bonded to the perimeter of the outer layer 80. However, it is not necessary for the entire elastic inner layer perimeter 25 to be bonded to the outer layer 80. The disposable garments 100 of the invention may have about 60% of the elastic inner layer perimeter 25 bonded to the outer layer 80. Likewise, about 80% of the elastic inner layer perimeter 25 may be bonded to the outer layer 80. The greater the percentage of the elastic inner layer perimeter 25 that is bonded to the outer layer 80, the better the elastic inner layer 20 controls the outer layer 80 during use. Another characteristic of the perimeter bonding is the percentage of bonded area, which may also be understood to represent the density of the bond pattern. The percentage of bonded area may be determined by measuring the bonded area, subtracting the area of the actual bonds, dividing the difference by the bonded area and multiplying by 100 to obtain the percentage of the bonded area that is not bonded. This percentage may then be subtracted from 100 to provide the percentage of bonded area. The percentage of bonded area may range from about 3% to about 70%. More specifically, the percentage of bonded area may range from about 7% to about 30% or from about 10% to about 20%. The perimeter bond may also be characterized by its width. Along the longitudinal side edges 55 of the garment 100, the width of the perimeter bond would be in a direction generally perpendicular to the longitudinal direction 60 of the garment 100. Along the waist edges 35 and 45 of the garment 100, the width of the perimeter bond would be in a direction generally perpendicular to the lateral direction 70 of the garment 100. The width of the perimeter bond may range from about 3 mm to about 50 mm. More specifically, the width of the perimeter bond may range from about 6 mm to about 25 mm or from about 12 mm to about 19 mm. Another characteristic of the perimeter bond is the location of the perimeter bond. The location of where the elastic inner layer perimeter 25 is bonded to the outer layer 80 may be next to or adjacent the garment perimeter. For example, an outward edge of the elastic inner layer perimeter 25 may be located within about 5 mm to about 25 mm from the garment perimeter.

The elastic inner layer perimeter 25 and the outer layer 80 may be bonded together using various techniques. As already described, the elastic inner layer perimeter 25 may be ultrasonically bonded to the outer layer 80. The shape of the bonding pattern may include a pattern anvil roll that takes the shape of the perimeter being bonded. An advantage of this method is that the bond pattern may also include a raised edge that permits the anvil roll to bond the two or more layers of materials, but also trims excess material that extends outward beyond the perimeter bond. The perimeter of the garment 100 may also be bonded with the use of pressure and heat. The shape of the bond pattern would be a pattern anvil roll and when the composite is run through the nip, the composite would be pressure bonded to the shape of the bond pattern. Additionally, the perimeter of the garment 100 may also be bonded with the use of adhesive. Desirably, the adhesive may be applied in a pattern that outlines the perimeter of the garment 100. The adhesives may be of a pressure-sensitive type or of a type that may be applied as a print adhesive.

The close-to-the-body fit and simplified construction of the disposable absorbent garments 100 of the invention may be provided in part, by the combination of the elastic inner layer 20 and the attachment of the absorbent assembly 150. The capacity of the disposable garments of the invention to contain bodily wastes may be provided by the combination of the opening 90 together with the manner in which the absorbent assembly 150 is attached to the elastic inner layer 20. When these features are combined, the disposable garments 100 of the invention unexpectedly provide excellent fit, minimal leakage and a simple garment construction that does not require the attachment of many individual components. Further, the elastic inner layer 20 separates the wearer's skin from the wastes contained by the absorbent assembly 150. By virtue of the absorbent assembly 150 being attached to the elastic inner layer 20 in the attachment regions 270 and other features, the garments 100 have a "light" or simplified "framework" or construction. Since the absorbent assembly 150 is laterally extensible, the absorbent assembly expands laterally along with the inner layer 20 so that expansion of the inner layer is generally uninhibited by attachment of the absorbent assembly thereto. This also allows void space formed by the absorbent assembly to expand upon expansion of inner layer 20 for retaining fecal matter while the garment maintains a good fit on the wearer. The material properties of the elastic inner layer 20 and the absence of the attachment of separate components in the front waist region 30 and the back waist region 40 provide garments 100 having a flexible waist closure or seal. Given the trend toward more complex disposable absorbent garments having more features and more components, the effectiveness of the garments 100 of the invention is unexpected.

Figure 11:
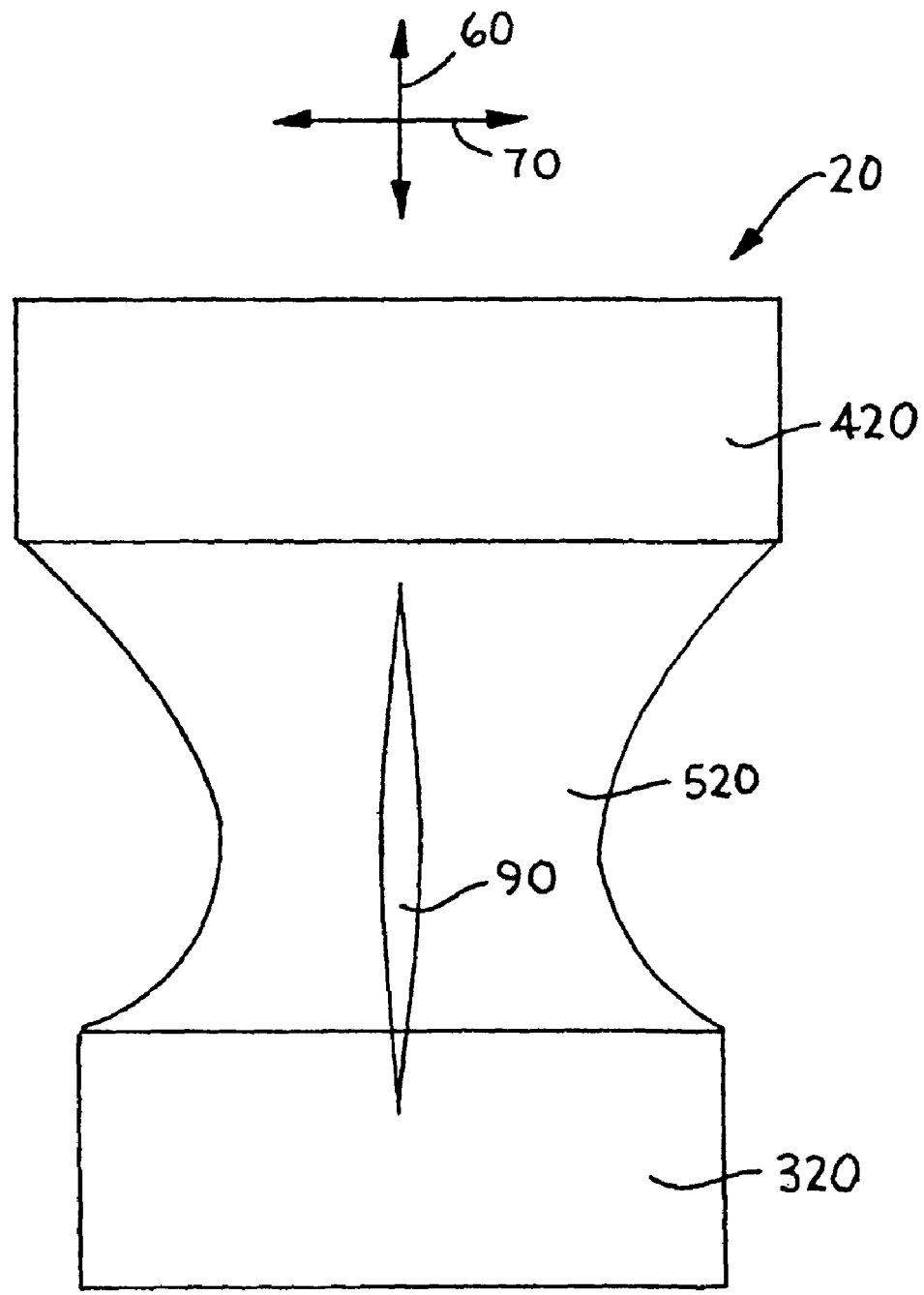
FIG. 11 representatively shows a plan view of an elastic inner layer of the invention that includes multiple sections.

While in the illustrated embodiment of FIG. 1 the elastic inner layer 20 is a continuous layer, it is contemplated that in other embodiments the disposable garment 100 may be constructed of an elastic inner layer 20 that is not continuous and is instead constructed of two or more discrete pieces to allow multi-direction stretching of the inner layer. Such a multiple piece construction of the elastic inner layer 20 creates the opportunity to provide garments 100 having stretch characteristics that are tailored for the various regions of the garments 100. For example, an elastic inner layer 20 may be provided that has a front waist region 30, a back waist region 40 and a crotch region 50 being elastically stretchable in different directions. FIG. 11 representatively illustrates an elastic inner layer 20 that includes a front piece 320, a back piece 420 and a crotch piece 520.

In a particular combination, the front piece 320 and the back piece 420 may be elastically stretchable in the lateral direction 70 while the crotch piece 520 is elastically stretchable in the longitudinal direction 60. The front piece 320 and the back piece 420 may be attached to the crotch piece 520 using adhesives or ultrasonic or thermal bonding. Alternatively, the crotch piece 520 may be elastically stretchable in the longitudinal direction 60 and extensible in the lateral direction 70. Other combinations are also possible. For example, the front piece 320 may be elastically stretchable in the lateral direction 70 while the back piece 420 and the crotch piece 520 are elastically stretchable in both the lateral direction 70 and the longitudinal direction 60. The opening 90 may be formed within only the crotch piece 520 or alternatively, the opening 90 may extend between the front piece 320, the back piece 420 and the crotch piece 520.

Figure 14:
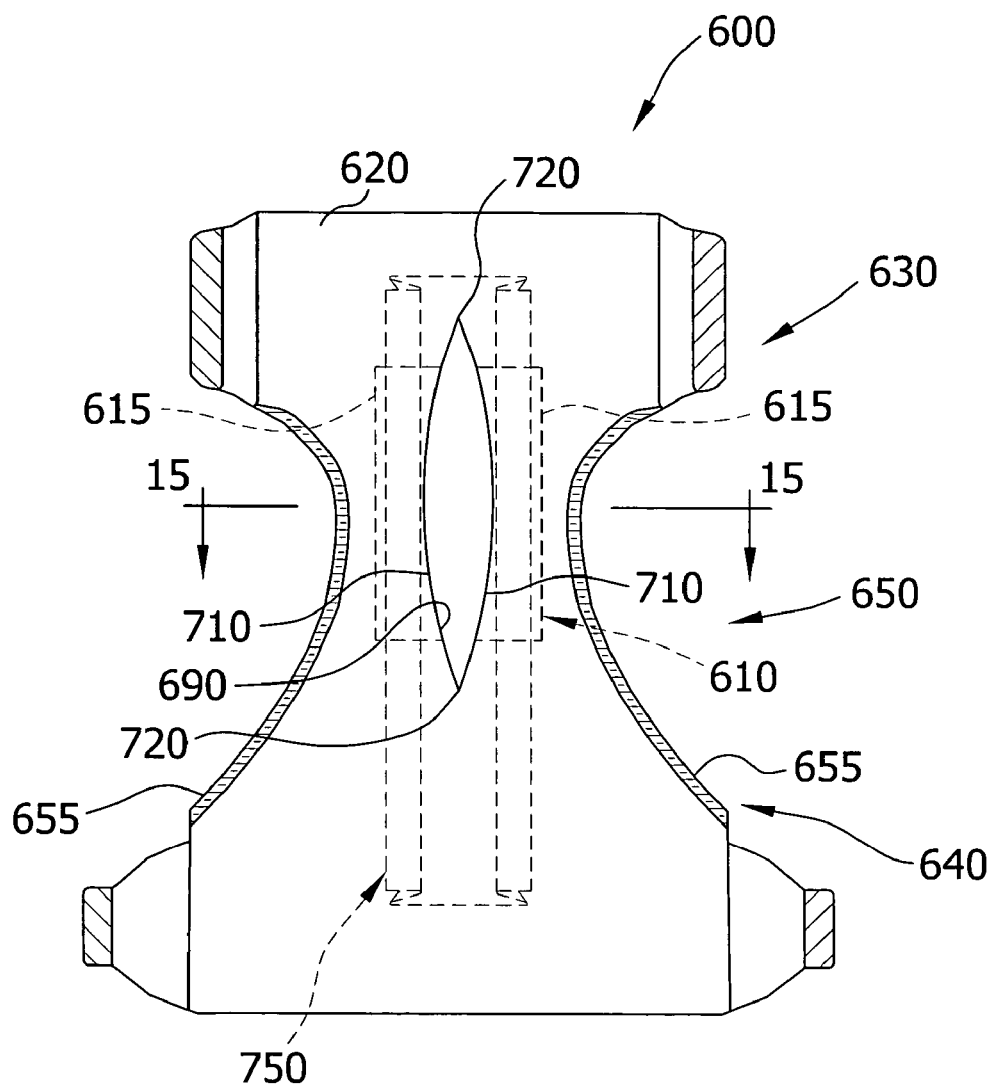
FIG. 14 representatively shows a plan view of the interior (body-facing) surface of another embodiment of a disposable absorbent garment of the present invention.
Figure 14:
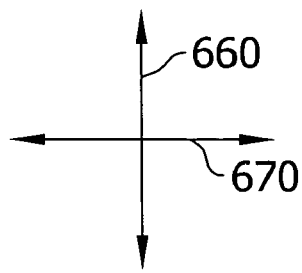

With reference now to FIG. 14, in another embodiment a disposable absorbent garment 600 comprises an elastic inner layer 620 constructed in a manner similar to the elastic inner layer 20 of the embodiment of FIGS. 1-8 and having an opening 690 therein similar to the opening 90 of the previous embodiments. For example, the opening 690 shown in FIG. 14 is an elongate aperture disposed within the crotch region 650 and extending into the front waist region 630. It is understood that the aperture may extend longitudinally from the crotch region 650 further into the back waist region 640 of the garment 600, or the aperture may be shorter than as shown in FIG. 14 and extend only within the crotch region of the garment. The length of the opening 690 contributes the lateral expansion (e.g., stretchability) of the elastic inner layer, with the lateral stretchability increasing with the length of the opening.

In this embodiment, a reinforcement element, generally indicated at 610, is secured to the elastic inner layer 620 along at least a portion of the opening 690 (e.g., at the periphery thereof) to reinforce the inner layer during stretching thereof at the opening. More suitably, the reinforcement element 610 is stretchable in at least the longitudinal direction 660 of the garment 600, and even more suitably the reinforcement element is elastic in at least the longitudinal direction of the garment. In such an embodiment, the elastic reinforcement element 610 also provides a measure of bias to the elastic inner layer 620 toward a generally relaxed configuration thereof at the opening 690 in the elastic inner layer to thereby inhibit overexpansion of the inner layer at the opening. In another embodiment, the reinforcement element 610 may be stretchable in both the lateral and longitudinal directions 660, 670, and more suitably it may be elastic in both the lateral and longitudinal directions.

The reinforcement element 610 may suitably be constructed of either a liquid permeable material or a liquid impermeable material. For example, where the elastic inner layer 620 is liquid permeable, the reinforcement element is suitably liquid permeable to allow liquid body waste to penetrate through the reinforcement element for flow to the absorbent assembly 750. Suitable elastic liquid permeable materials include those described previously as being suitably for forming the elastic inner layer 20 of FIG. 1. Where the elastic inner layer 620 is liquid impermeable, the reinforcement element is suitably liquid impermeable but may also be liquid permeable. Suitable elastic liquid impermeable materials include those described previously for forming a liquid impermeable elastic inner layer 20 of FIG. 1.

Figure 18:
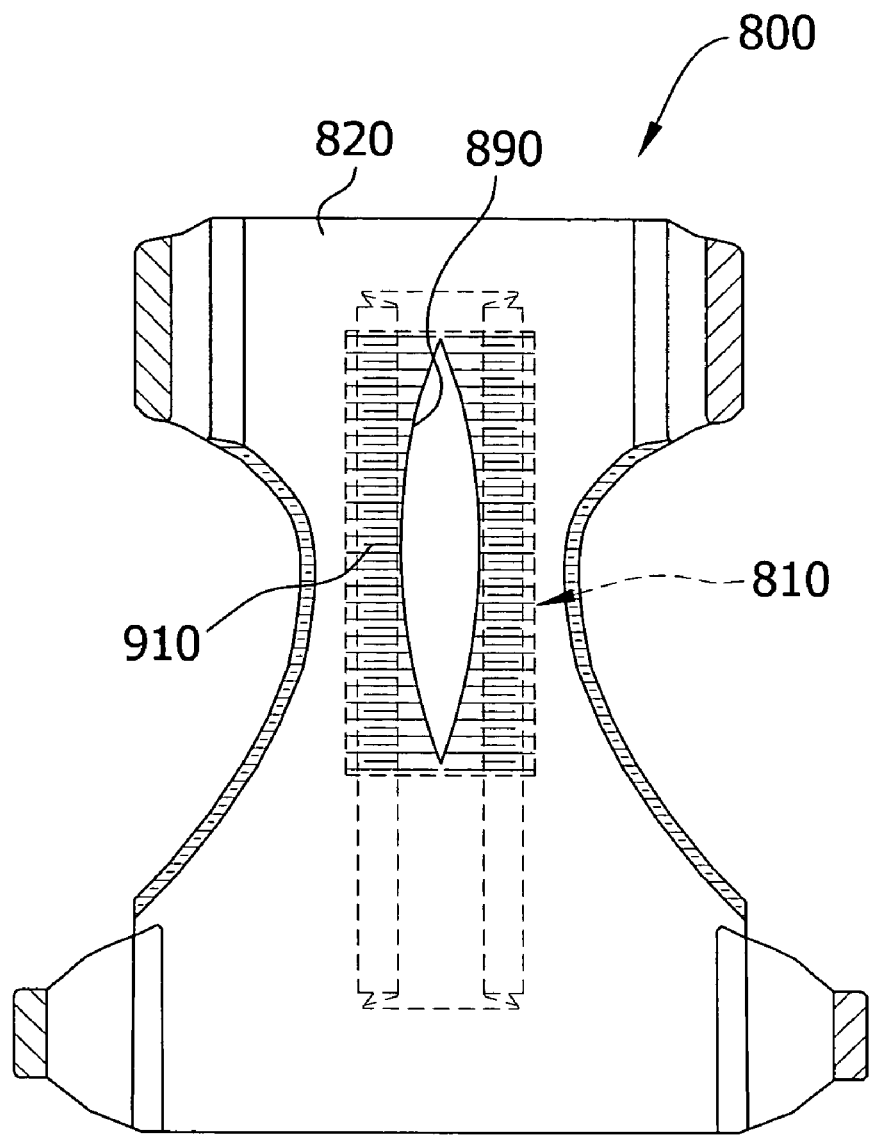
FIG. 18 representatively shows a plan view of the interior (body-facing) surface of a fourth embodiment of a disposable absorbent garment of the present invention.
Figure 18:
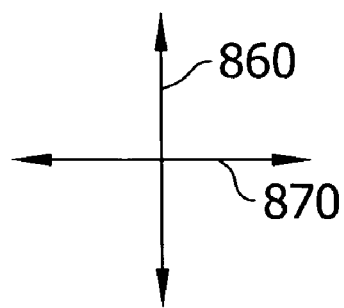

In the illustrated embodiment of FIG. 14, the reinforcement element 610 is of two piece construction, with separate, laterally spaced pieces 615 extending longitudinally along laterally opposite sides 710 of the inner layer opening 690. Specifically, each reinforcement element piece 615 extends longitudinally from a location longitudinally inward of one end 720 of the opening 690 to a location longitudinally inward from the opposite end 720 of the opening. However, it is contemplated that the reinforcement element 610 may instead extend beyond one or both ends of the opening 690, and may completely surround the opening as shown in the alternative embodiment of FIG. 18. It is also understood that where the reinforcement element 610 surrounds the opening 690, the reinforcement element may suitably be of single-piece construction, e.g, with an opening formed therein corresponding to the opening in the elastic inner layer 620.

Figure 15:
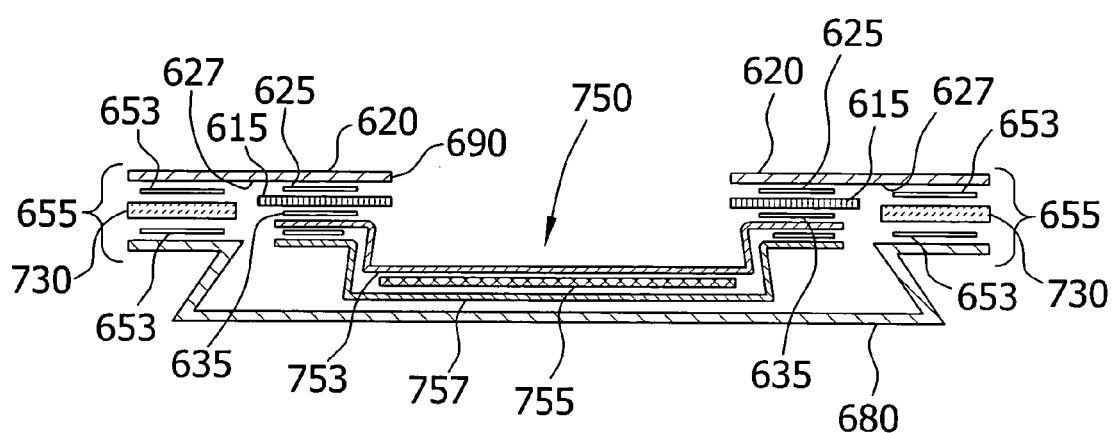
FIG. 15 is a schematic cross-section taken in the plane of line 15-15 of FIG. 14.

The reinforcement element 610 (e.g., pieces 615 in FIG. 15) is suitably secured to the exterior surface 627 of the elastic inner layer 620 by adhesive 625. However, other suitable bonding techniques, such as ultrasonic bonding or thermal bonding, may be used to secure the reinforcement element 610 to the inner layer without departing from the scope of this invention. It is also contemplated that the reinforcement element 610 may instead be secured to the interior (e.g., body-facing) surface of the elastic inner layer 620 and remain within the scope of this invention.

Figure 19:
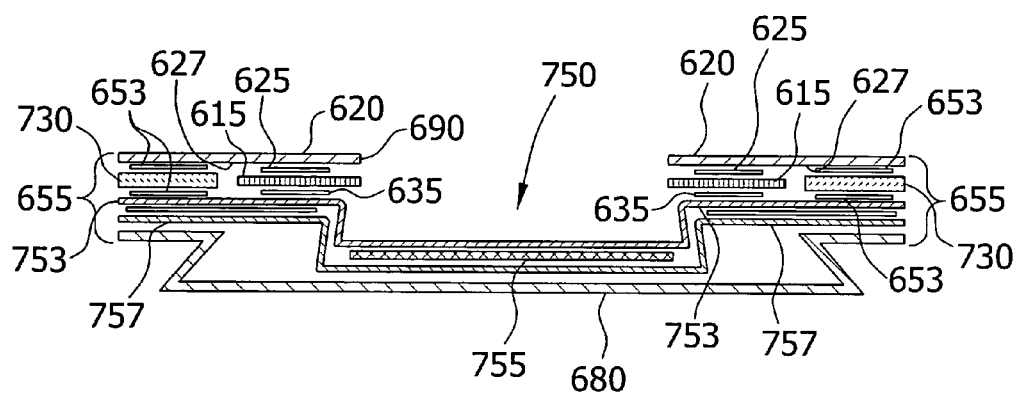
FIG. 19 is a schematic cross-section similar to that of FIG. 15 but taken of a fifth embodiment of a disposable absorbent garment of the present invention.

The garment 600 also includes laterally opposite leg elastic members 730 (FIG. 15) extending longitudinally along the side edges 655 of the garment. The leg elastic members 730 are suitably secured between the inner layer 620 and the outer layer 680, such as by being bonded to the inner layer and/or the outer layer by the laminate adhesive 653. However, it is understood that the absorbent assembly 750 (e.g., the barrier layer 757, the topsheet layer 753, or both) may extend laterally to the side edges 655 of the garment 600 as illustrated in the alternative embodiment of FIG. 19, and that leg elastic members 730 may be secured between the inner layer 620 and the absorbent assembly as shown in FIG. 19, and/or between the outer layer 680 and the absorbent assembly. A wide variety of elastic materials may be used for the leg elastic members 730. As is well known to those skilled in the art, suitable elastic materials include ribbons (as shown in the illustrated embodiment), sheets or strands of natural rubber, synthetic rubber, or thermoplastic elastomeric polymers. The leg elastic members 730 are suitably adhered to the inner and/or outer layers 620, 680 while in a stretched condition so that upon relaxing of the elastic members the lateral side edges 655 of the garment 600 become gathered as illustrated in FIG. 14. Alternatively, the inner and outer layers 620, 680 may be gathered and the elastic members 730 secured thereto in a generally relaxed condition, or the elastic members may be adhered to the inner and outer layers and then elasticized or shrunk, for example with the application of heat, such that elastic retractive forces are imparted to the lateral side edges 655 of the garment 600.

The absorbent assembly 750 is suitably similar to the extensible absorbent assembly 150 of FIG. 8 and is secured to the exterior surface 627 of the elastic inner layer 620 in opposed, underlying relationship with the opening 690. In particular, the absorbent assembly 750 is sized laterally wider than the opening 690 and extends longitudinally beyond both ends 720 of the opening. In the illustrated embodiment, the absorbent assembly 750 extends into the back waist region 640 of the garment 600 well beyond the end 720 of the opening 690 disposed toward the back waist region. It is contemplated, however, that the absorbent assembly 750 may extend only marginally beyond the end 720 of the opening 690 without departing from the scope of this invention. Along the longitudinal extent of the exterior surface 627 of the inner layer 620 to which the reinforcement element is adhered, the absorbent assembly 750 is secured to the reinforcement layer, such as by suitable adhesive 635 (FIG. 15) or other bonding technique, to thereby secure the absorbent assembly to the elastic inner layer. It is contemplated that instead of the absorbent assembly 750 being secured to the exterior surface 627 of the elastic inner layer 620, the lateral side edges of the absorbent assembly may extend up through the opening 690 and be secured to the interior surface of the inner layer without departing from the scope of this invention. The garment 600 also comprises the extensible outer layer 680 which is similar to the extensible outer layer 80 described previously in connection with the embodiments of FIGS. 1-8 as being secured to the inner layer 20 at the perimeter of the garment.

Figure 16:
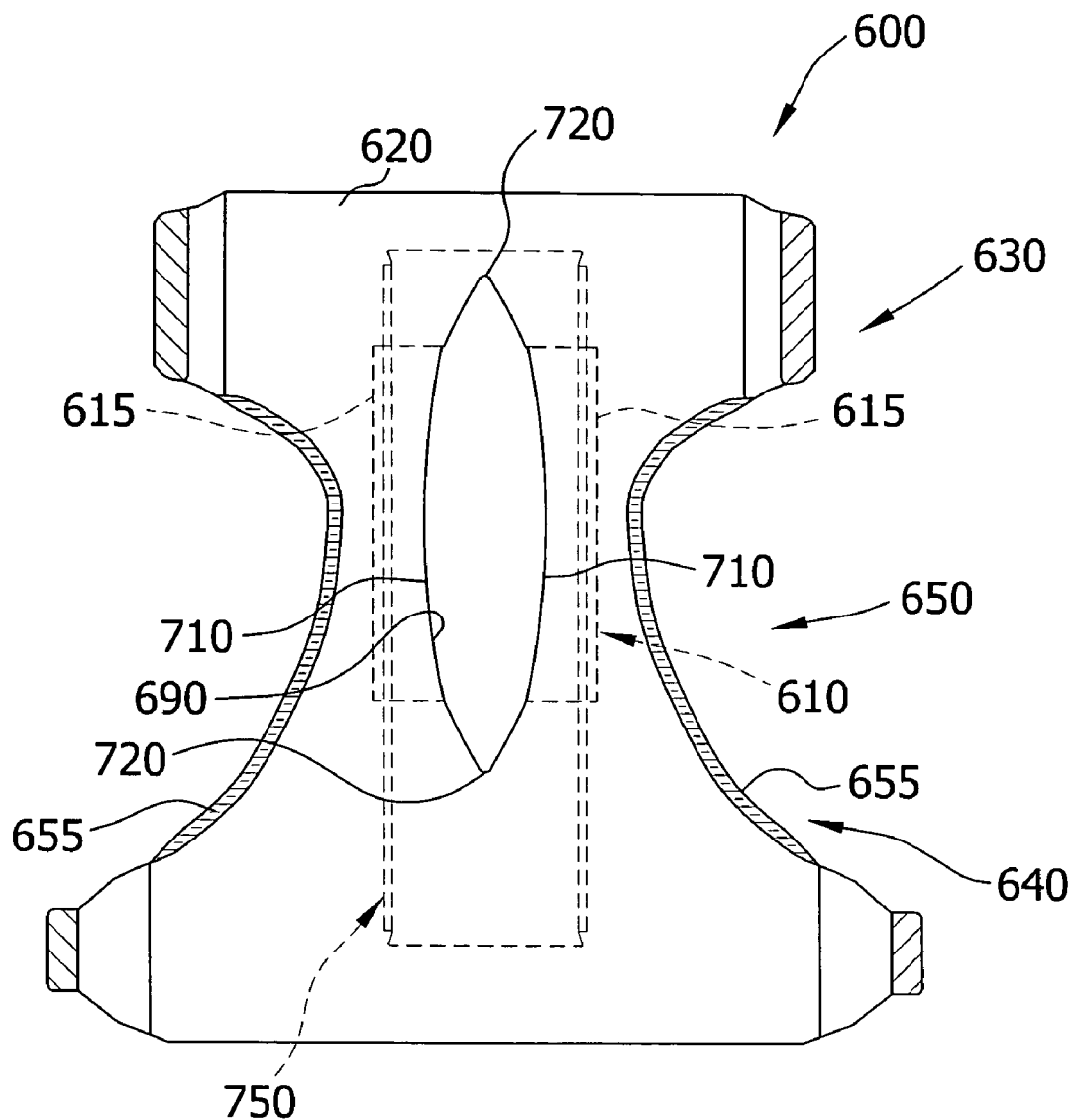
FIG. 16 representatively shows the garment of FIG. 14 in a laterally stretched condition.

In use, when lateral elongating forces are applied to the garment 600, such as upon initial donning of the garment or during wear (e.g., upon movement by the wearer or loading of the garment), the opening 690 formed in the elastic inner layer 620 facilitates lateral expansion of the inner layer at the crotch region 650, thereby allowing the entire garment to be stretched laterally to a stretched condition as shown in FIG. 16. In the stretched condition, the leg elastic members 730 are moved laterally outward as well and the contours of the lateral side edges 655 of the garment 600 are more pronounced so that the garment has a more comfortable fit on the wearer during stretching of the garment. Because the opposite sides of the absorbent assembly 750 are secured to the elastic inner layer 620, the absorbent assembly expands with the inner layer, thereby increasing the size of the void space defined by the absorbent assembly below the opening 690.

Figure 17:
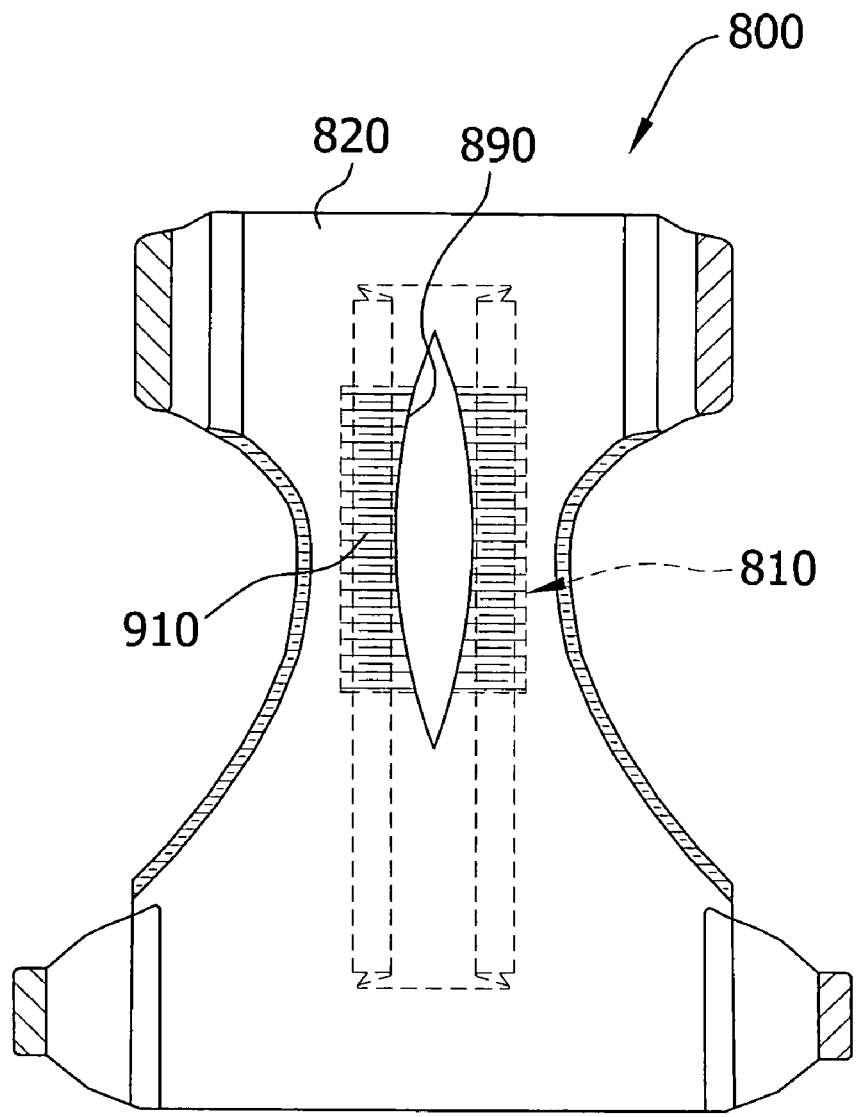
FIG. 17 representatively shows a plan view of the interior (body-facing) surface of a third embodiment of a disposable absorbent garment of the present invention.
Figure 17:
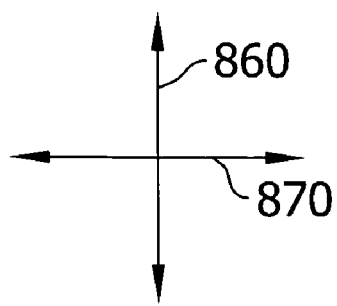

FIG. 17 illustrates another embodiment of a disposable absorbent garment 800 that is similar to the garment 600 of FIG. 14. The garment 800 of this embodiment includes an elastic reinforcement element 810 that is elastic at least in the longitudinal direction 860 of the garment and more suitably in both the longitudinal and lateral directions of the garment. The elastic reinforcement element 810 is suitably secured to the elastic inner layer 820 (e.g., to the exterior surface of the elastic inner layer) while the reinforcement element is elastically stretched in the longitudinal direction 860 of the garment 800 so that relaxing of the reinforcement element forms gathers 910 in the inner layer along the longitudinal extent of the reinforcement element as shown in FIG. 17. In the alternative embodiment shown in FIG. 18, the reinforcement element 810 completely surrounds the opening 890 formed in the inner layer so that the gathers 910 are disposed along the entire length of the opening. The gathers 910 in each of these embodiments allow the inner layer 820 to maintain a comfortable fit against the wearer upon longitudinal expansion of the garment during use, such as upon loading of the absorbent assembly.

While the disposable absorbent garments of the invention have been described in detail with respect to specific aspects thereof, it will be appreciated that those skilled in the art, upon attaining an understanding of the foregoing, may readily conceive of alterations to, variations of and equivalents to these garments. Accordingly, the scope of the present invention should be assessed as that of the appended claims and any equivalents thereto.

What is claimed is:

1. A disposable absorbent garment, the disposable absorbent garment having a longitudinal direction, a lateral direction, a front waist region, a back waist region and a crotch region extending longitudinally between and interconnecting the front waist region and the back waist region, longitudinal ends and lateral side edges, the disposable absorbent garment comprising:

an elastic inner layer having an interior surface for facing a wearer of the garment, and an exterior surface, the elastic inner layer having an elongate opening therein disposed at least within the crotch region of the garment, said elastic inner layer being stretchable in at least the lateral direction of the garment;

an outer layer in opposed relationship with the elastic inner layer, said outer layer being stretchable in at least the lateral direction of the garment; and an absorbent assembly disposed between the elastic inner layer and the outer layer for receiving body waste that passes through the elastic inner layer, the absorbent assembly being secured to the elastic inner layer and being sized larger than said opening of said elastic inner layer for underlying substantially the entire opening, said absorbent assembly being stretchable in at least the lateral direction of the garment for lateral stretching thereof in response to lateral stretching of the elastic inner layer.

2. The disposable absorbent garment set forth in claim 1 wherein the absorbent assembly is secured to the exterior surface of the elastic inner layer.

3. The disposable absorbent garment set forth in claim 1 wherein the opening of the elastic inner layer has longitudinally opposite ends and laterally opposite side edges, the absorbent assembly extending generally longitudinally beyond each of said longitudinal ends of the opening and extending generally laterally beyond the lateral side edges of said opening, said absorbent assembly having lateral side edges secured to the elastic inner layer generally laterally outward of the lateral side edges of said opening.

4. The disposable absorbent garment set forth in claim 1 wherein the garment has a length in the longitudinal direction thereof, the opening in the elastic inner layer having a length in the longitudinal direction in the range of about 10 percent to about 90 percent of the garment length.

5. The disposable absorbent garment set forth in claim 4 wherein the length of the elastic inner layer is in the range of about 25 percent to about 50 percent of the garment length.

6. The disposable absorbent garment set forth in claim 1 wherein the opening in the elastic inner layer extends longitudinally from the crotch region into at least one of the front waist region and the back waist region of the garment.

7. The disposable absorbent garment set forth in claim 6 wherein the opening in the elastic inner layer extends longitudinally from the crotch region into each of the front waist region and the back waist region of the garment.

8. The disposable absorbent garment set forth in claim 1 wherein the opening comprises a slit formed in the elastic inner layer.

9. The disposable absorbent garment set forth in claim 1 wherein the opening comprises an elongate aperture formed in the elastic inner layer.

10. The disposable absorbent garment set forth in claim 9 wherein the interior surface of the elastic inner layer has a surface area, the opening defining an open area in the range of about 5 percent to about 25 percent of the surface area of the interior surface of the elastic inner layer.

11. The disposable absorbent garment set forth in claim 1 wherein the absorbent assembly comprises a liquid permeable topsheet layer, a barrier layer in opposed relationship with the topsheet layer, and an absorbent core layer disposed between the topsheet layer and the barrier layer.

12. The disposable absorbent garment set forth in claim 1 wherein the elastic inner layer is elastic in both the longitudinal direction and the lateral direction of said garment.

13. The disposable absorbent garment set forth in claim 1, wherein the elastic inner layer is liquid impermeable.

14. The disposable absorbent garment set forth in claim 1, wherein the elastic inner layer comprises at least two layers secured together.

15. The disposable absorbent garment set forth in claim 1 further comprising a reinforcement element secured to the elastic inner layer generally at the opening thereof.

16. The disposable absorbent garment set forth in claim 15 wherein the opening has laterally opposite side edges extending longitudinally along a length of the opening, the reinforcement element extending longitudinally adjacent each of the laterally opposite side edges of the opening along at least a portion of the length of said opening.

17. The disposable absorbent garment set forth in claim 15 wherein the reinforcement element substantially surrounds the opening of the elastic inner layer.

18. The disposable absorbent garment set forth in claim 15 wherein the reinforcement element is elastic, said reinforcement element being stretchable in at least one of the longitudinal direction and the lateral direction of the garment.

19. The disposable absorbent garment set forth in claim 18 wherein the elastic reinforcement element is secured the inner layer to gather the inner layer at the opening thereof generally in the longitudinal direction of the garment.

20. The disposable absorbent garment set forth in claim 1 further comprising laterally opposite leg elastic members extending longitudinally generally along the lateral side edges of the garment.

21. A disposable absorbent garment, the disposable absorbent garment having a longitudinal direction, a lateral direction, a front waist region, a back waist region and a crotch region extending longitudinally between and interconnecting the front waist region and the back waist region, longitudinal ends and lateral side edges, the disposable absorbent garment comprising:

an elastic inner layer having an interior surface for facing a wearer of the garment, and an exterior surface, the elastic inner layer having an elongate opening therein disposed at least within the crotch region of the garment, said elastic inner layer being stretchable in at least the lateral direction of the garment; and an absorbent assembly secured to the elastic inner layer, the absorbent assembly being sized larger than the opening of said elastic inner layer and underlying substantially the entire opening, said absorbent assembly comprising a liquid permeable topsheet layer, a barrier layer in opposed relationship with the topsheet layer, and an absorbent core layer disposed between the topsheet layer and the barrier layer, said absorbent assembly being stretchable in at least the lateral direction for lateral stretching of the absorbent assembly in response to lateral stretching of the elastic inner layer.

22. The disposable absorbent garment set forth in claim 20 wherein the absorbent assembly is secured to the exterior surface of the elastic inner layer.

23. The disposable absorbent garment set forth in claim 20 wherein the opening of the elastic inner layer has longitudinally opposite ends and laterally opposite side edges, the absorbent assembly extending generally longitudinally beyond each of said longitudinal ends of the opening and extending generally laterally beyond the lateral side edges of said opening, said absorbent assembly having lateral side edges secured to the elastic inner layer generally laterally outward of the lateral side edges of said opening.

24. The disposable absorbent garment set forth in claim 1 wherein the garment has a length in the longitudinal direction thereof, the opening in the elastic inner layer having a length in the longitudinal direction in the range of about 10 percent to about 90 percent of the garment length.

25. The disposable absorbent garment set forth in claim 20 wherein the opening in the elastic inner layer extends longitudinally from the crotch region into at least one of the front waist region and the back waist region of the garment.

26. The disposable absorbent garment set forth in claim 20 wherein the opening comprises a slit formed in the elastic inner layer.

27. The disposable absorbent garment set forth in claim 20 wherein the opening comprises an elongate aperture formed in the elastic inner layer.

28. The disposable absorbent garment set forth in claim 20 wherein the elastic inner layer is elastic in both the longitudinal direction and the lateral direction of said garment.

29. The disposable absorbent garment set forth in claim 20, wherein the elastic inner layer is liquid impermeable.

30. The disposable absorbent garment set forth in claim 20 further comprising a reinforcement element secured to the elastic inner layer generally at the opening thereof.

31. The disposable absorbent garment set forth in claim 30 wherein the opening has laterally opposite side edges extending longitudinally along a length of the opening, the reinforcement element extending longitudinally adjacent each of the laterally opposite side edges of the opening along at least a portion of the length of said opening.

32. The disposable absorbent garment set forth in claim 30 wherein the reinforcement element substantially surrounds the opening of the elastic inner layer.

33. The disposable absorbent garment set forth in claim 30 wherein the reinforcement element is elastic, said reinforcement element being stretchable in at least one of the longitudinal direction and the lateral direction of the garment.

34. The disposable absorbent garment set forth in claim 33 wherein the elastic reinforcement element is secured the inner layer to gather the inner layer at the opening thereof generally in the longitudinal direction of the garment.

35. The disposable absorbent garment set forth in claim 20 wherein the absorbent assembly has laterally opposite side edges at least in part defining the lateral side edges of the garment.

36. The disposable absorbent garment set forth in claim 35 further comprising laterally opposite leg elastic members extending longitudinally generally adjacent the lateral side edges of the garment.

37. The disposable absorbent garment set forth in claim 36 wherein the leg elastic members are disposed between the elastic inner layer and the absorbent assembly.

38. A disposable absorbent garment, the disposable absorbent garment having a longitudinal direction, a lateral direction, a front waist region, a back waist region and a crotch region extending longitudinally between and interconnecting the front waist region and the back waist region, longitudinal ends and lateral side edges, the disposable absorbent garment comprising:

an elastic inner layer having an interior surface for facing a wearer of the garment, and an exterior surface, the elastic inner layer having an elongate opening therein disposed at least within the crotch region of the garment, said elastic inner layer being stretchable in at least the lateral direction of the garment;

an outer layer in opposed relationship with the elastic inner layer, said outer layer being stretchable in at least the lateral direction of the garment;

an absorbent assembly disposed between the elastic inner layer and the outer layer for receiving body waste that passes through the elastic inner layer, the absorbent assembly being secured to the elastic inner layer and being sized larger than said opening of said elastic inner layer for underlying substantially the entire opening, said absorbent assembly being stretchable in at least the lateral direction of the garment for lateral stretching thereof in response to lateral stretching of the elastic inner layer;

at least one leg elastic member generally adjacent each of the laterally opposite side edges of the garment and extending longitudinally along said garment side edges; and a reinforcement element secured to the elastic inner layer generally at the opening thereof and being elastic in at least the lateral direction of the garment.

* * * * *